United States Patent
Amari et al.

(10) Patent No.: US 9,597,323 B2
(45) Date of Patent: Mar. 21, 2017

(54) AMINOESTER DERIVATIVES

(71) Applicant: CHIESI FARMACEUTICI S.p.A., Parma (IT)

(72) Inventors: Gabriele Amari, Parma (IT); Elisabetta Armani, Parma (IT); Herve Van De Poeol, Saffron Walden (GB); Charles Baker-Glenn, Saffron Walden (GB); Naimisha Trivedi, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/168,438

(22) Filed: May 31, 2016

(65) Prior Publication Data

US 2016/0346260 A1 Dec. 1, 2016

(30) Foreign Application Priority Data

Jun. 1, 2015 (EP) ..................................... 15170047

(51) Int. Cl.
| | | |
|---|---|---|
| *A61K 31/444* | (2006.01) | |
| *C07D 401/12* | (2006.01) | |
| *A61K 31/452* | (2006.01) | |
| *C07D 453/02* | (2006.01) | |

(52) U.S. Cl.
CPC .......... *A61K 31/444* (2013.01); *A61K 31/452* (2013.01); *C07D 401/12* (2013.01); *C07D 453/02* (2013.01)

(58) Field of Classification Search
None
See application file for complete search history.

(56) References Cited

U.S. PATENT DOCUMENTS

| | | | |
|---|---|---|---|
| 2013/0079313 A1* | 3/2013 | Armani ................ | C07D 213/89 514/171 |
| 2013/0324501 A1* | 12/2013 | Armani ................ | C07D 401/12 514/158 |
| 2014/0155391 A1* | 6/2014 | Armani .............. | C07D 295/155 514/227.8 |
| 2015/0158858 A1* | 6/2015 | Amari .................. | C07D 409/14 514/210.2 |
| 2015/0352091 A1* | 12/2015 | Armani ................ | C07D 409/14 514/305 |

FOREIGN PATENT DOCUMENTS

| | | |
|---|---|---|
| WO | 2012168226 | * 12/2012 |
| WO | 2013057013 | * 4/2013 |
| WO | 2013182451 | * 12/2013 |
| WO | 2014/086849 | 6/2014 |

OTHER PUBLICATIONS

Extended European Search Report in Application No. 15170047.3 dated Aug. 18, 2015.
Asthma: U.S. FDS approves new indication for SPIRIVA Respimat, (2016).
X. Soler et al., Curr Allergy Asthma Rep (2014) 14:484.
Clinical Trails.gov, NCT00073177 (2012).
Clinical Trails.gov, NCT00076076 (2012).
Clinical Trails.gov, NCT00163527 (2012).

* cited by examiner

*Primary Examiner* — Karl J Puttlitz
(74) *Attorney, Agent, or Firm* — Oblon, McClelland, Maier & Neustadt, L.L.P.

(57) ABSTRACT

Compounds of formula (I) defined herein are both phosphodiesterase 4 (PDE4) enzyme inhibitors and muscarinic M3 receptor antagonists and are useful for treating diseases of the respiratory tract.

17 Claims, No Drawings

AMINOESTER DERIVATIVES

CROSS REFERENCES TO RELATED APPLICATIONS

This application claims priority to European Patent Application No. 15170047.3, filed on Jun. 1, 2015, which is incorporated herein by reference in its entirety.

BACKGROUND OF THE INVENTION

Field of the Invention

The present invention relates to novel compounds which are both phosphodiesterase 4 (PDE4) enzyme inhibitors and muscarinic M3 receptor antagonists. The present invention further relates to methods of preparing such a compound, compositions which contain such a compound, therapeutic uses of such a compound.

Discussion of the Background

Chronic obstructive pulmonary disease (COPD) is a respiratory disorder characterized by progressive, not fully reversible, airflow limitation associated with an abnormal pulmonary inflammatory response to noxious particles or gases.

For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into two general classes: bronchodilators, (β2-adrenoceptor agonists, antimuscarinic agents and methylxanthines) and antiinflammatory agents (glucocorticosteroids and selective phosphodiesterase-4 (PDE4) inhibitors).

Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors.

Currently, there are five known muscarinic receptor subtypes (M1-M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells.

These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors, the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over four weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

WO 2014/086852, WO 2014/086849, WO 2014/086855, WO 2015/082616, and WO 2015/082619, all of which are incorporated herein by reference in their entireties, disclose compounds with both bronchodilating and antiinflammatory properties.

However, there remains a need for additional compounds which exhibit both bronchodilating and antiinflammatory properties.

SUMMARY OF THE INVENTION

Accordingly, it is one object of the present invention to provide novel compounds which act both as inhibitors of the phosphodiesterase 4 (PDE4) enzyme and as muscarinic M3 receptor antagonists.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery that compounds of formula (I):

(I)

wherein
each $R_1$ is hydrogen or is independently selected from the group consisting of: halogen, $(C_1-C_4)$ alkyl, $(C_1-C_4)$ alkoxy, $(C_1-C_4)$ haloalkyl, hydroxy, —$SO_2NR_6R_7$, —CN, —$NR_8SO_2R_9$, —$NR_6R_7$, —$CONR_6R_7$ and —$NR_8COR_9$ and wherein said $(C_1-C_4)$ alkyl is optionally substituted by one or more groups selected from $(C_3-C_7)$ cycloalkyl, hydroxy and —$NR_6R_7$ and wherein said $(C_1-C_4)$ alkoxy is optionally substituted by one or more halogens or groups $(C_3-C_7)$ cycloalkyl, wherein $R_6$ is hydrogen or $(C_1-C_6)$ alkyl;
$R_7$ is hydrogen or $(C_1-C_6)$ alkyl;
$R_8$ is hydrogen or $(C_1-C_6)$ alkyl;
$R_9$ is hydrogen or $(C_1-C_6)$ alkyl;
n is an integer ranging from 1 to 3;
each $R_2$ is hydrogen or is selected from the group consisting of halogen, $(C_1-C_4)$ alkyl, $(C_1-C_4)$ alkoxy, $(C_1-C_4)$ haloalkyl, hydroxy, —$SO_2NR_1OR_{11}$, —CN and —$NR_{12}SO_2R_{13}$ and wherein said $(C_1-C_4)$ alkyl and said $(C_1-C_4)$ alkoxy are optionally substituted by one or more group $(C_3-C_7)$ cycloalkyl, wherein
$R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
m is an integer ranging from 1 to 3;
$R_3$ and $R_4$ are different or the same and are independently selected from the group consisting of: H, $(C_3-C_7)$ cycloalkylcarbonyl, $(C_1-C_6)$ alkyl optionally substituted by one or more substituents selected from $(C_1-C_4)$ alkoxy, $(C_3-C_7)$ cycloalkyl or $(C_5-C_7)$ cycloalkenyl, $(C_1-C_6)$ haloalkyl, $(C_3-C_7)$ cycloalkyl, $(C_5-C_7)$ cycloalkenyl, $(C_2-C_6)$ alkenyl, and $(C_2-C_6)$ alkynyl;
each $R_5$, whenever present, is independently selected from the group consisting of: CN, $NO_2$, $CF_3$ and halogen atoms;
k is 0 or an integer ranging from 1 to 3;
$W_1$ is selected from a divalent arylene group;
$W_2$ is selected from an aryl and a heteroaryl or $(C_3-C_7)$ cycloalkyl;
L is a bond or a —$(CH_2)$— group;
$L_1$ is selected from the list consisting of: a bond, —$(CH_2)_p$—, [3]-$(CH_2)_p$—O-[4], [3]-$(CH_2)_p$—$NR_{10}$—$(CH_2)_t$-[4], [3]-$(CH_2)_p$—OC(O)-[4], [3]-$(CH_2)_p$—$NR_{10}$C(O)-[4], [3]-$(CH_2)_p$—$NR_{10}$S($O_2$)-[4], and [3]-$(CH_2)_p$—S($O_2$)—N($R_{10}$)-[4],
wherein [3] and [4] represent, respectively the point of attachment of group $L_1$ to the carbonyl group and to the ring $W_1$ and wherein
$R_{10}$ is as described above,
p is an integer ranging from 1 to 4 and
t is an integer ranging from 1 to 4;
$L_2$ is a group selected from —$(CH_2)_q$— wherein q is an integer ranging from 1 to 4;
$L_3$ is a $(C_1-C_4)$ alkylene;
X is a group selected from $X_1$, $X_2$ and $X_3$:

$X_1$ $X_2$

-continued

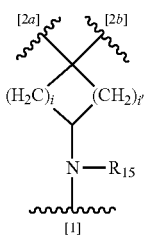

wherein [1], represent in each occurrence the point of attachment of the group X to L2, [2a] the point of attachment to L-W$_2$ and [2b] the point of attachment to the carbonyl group —CO$_2$A;

and wherein

R$_{14}$ is selected from the group consisting of H, OH, (C$_1$-C$_4$) alkyl, (C$_1$-C$_4$) alkoxy, (C$_1$-C$_4$) haloalkyl, and —CN, wherein said (C$_1$-C$_4$) alkyl is optionally substituted by one or more groups selected from (C$_3$-C$_7$) cycloalkyl and hydroxyl, or, in alternative, when R$_{14}$ is (C$_1$-C$_4$) alkyl, W$_2$ is a phenyl ring, one of R$_1$ is an alkyl in ortho position with respect to L, both R$_1$ and R$_{14}$ may be connected to form with W$_2$ a condensed ring radical selected from at least 1H-cyclopropabenzene-1,1-diyl, indane-1,1-diyl (also named as 2,3-dihydro-1H-indene-1,1-diyl), indane-2,2-diyl (also named as 2,3-dihydro-1H-indene-2,2-diyl), 1,2,3,4-tetrahydronaphthalene-1,1-diyl, and 1,2,3,4-tetrahydronaphthalene-2,2-diyl;

R$_{15}$ is selected from hydrogen, (C$_1$-C$_6$) alkyl, (C$_3$-C$_7$) cycloalkyl, (C$_3$-C$_7$) heterocycloalkyl and benzyl; wherein said (C$_1$-C$_6$) alkyl is optionally substituted by hydroxyl or NR$_{18}$R$_{19}$; said R$_{18}$ and R$_{19}$ being independently selected from hydrogen and (C$_1$-C$_4$) alkyl, or, taken together with the nitrogen atom to which they are attached, form a nitrogen containing, saturated heterocycloalkyl group, optionally containing an additional heteroatom selected from O, S and NH;

and wherein i is 1 or 2;

i' is 1 or 2;

i'' is an integer ranging from 0 to 3;

A is selected from the groups of formula (i) to (v):

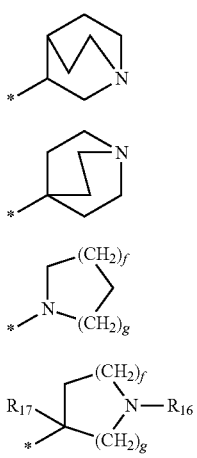

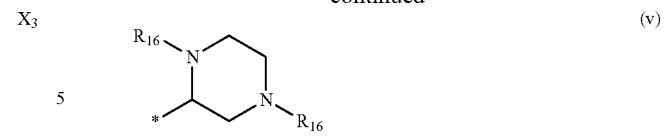

wherein R$_{16}$ is in each occurrence independently selected from (C$_1$-C$_4$) alkyl optionally substituted by one or more (C$_1$-C$_4$) alkoxy groups; R$_{17}$ is hydrogen, halogen or (C$_1$-C$_4$) alkyl; f=0, 1, 2 or 3; g=0, 1, 2 or 3; and the asterisk (*) represents the point of attachment to the group L$_3$ in formula (I);

their N-oxides on the pyridine ring, deuterated derivatives, pharmaceutically acceptable salts, and solvates thereof, act both as inhibitors of the phosphodiesterase 4 (PDE4) enzyme and as muscarinic M3 receptor antagonists.

The present invention further provides the corresponding N-oxides on the pyridine ring of compounds of formula (I) which are represented by the formula (I)'

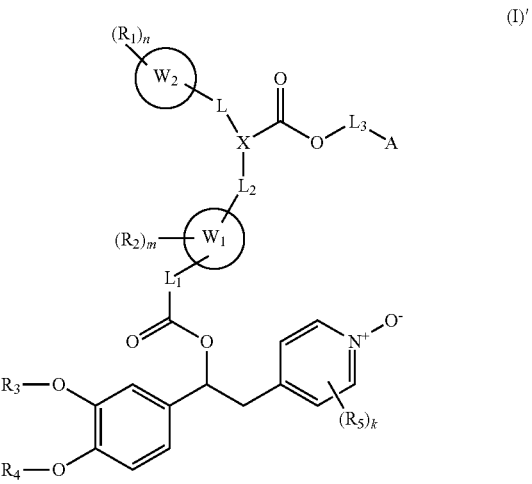

wherein R$_1$, R$_2$, R$_3$, R$_4$, R$_5$, L, L$_1$, W$_1$, L$_2$, W$_2$, X, L$_3$, A, m, n, and k are as described above.

The present invention further concerns the corresponding deuterated derivatives of compounds of formula (I) wherein at least one hydrogen atom is substituted by corresponding atoms of deuterium.

In the context of the present invention, the term deuterated derivative means that the at least one position occupied by a hydrogen atom is occupied by deuterium in an amount above its natural abundance. Preferably, the percent of deuterium at that position is at least 90%, more preferably at least 95%, even more preferably 99%. Preferably deuterated derivatives according to the invention are deuterated at available positions in the substituent R$_3$.

The present invention also provides the pharmaceutically acceptable salts and/or solvates thereof.

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable.

Suitable examples of said salts may include mineral or organic acid addition salts of basic residues such as amino groups, as well as mineral or organic acid residues such as carboxylic groups.

Cations of inorganic bases which can be suitably used to prepare salts within the present invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

The skilled person will appreciate that many organic compounds can form complexes with solvents in which they are reacted or from which they are precipitated or crystallized. These complexes are known as "solvates." Pharmaceutically acceptable solvates of compound of the invention are within the scope of the present invention.

Included within the scope of the present invention are also polymorphs and crystalline forms of compounds of formula (I), of their N-oxides on the pyridine ring, or of pharmaceutically acceptable salts, or solvates thereof Hereinafter, compounds of formula (I), (IA), (IB), (IC), (ID), (Ia), (Ib), (Ic), (Id) (Ie), (If), (Ig), (Ih), (Ii), (ID, (Im), (In), (I'), and (I)", corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention."

The present invention further comprises a process for the preparation of compounds of the invention.

The present invention also provides pharmaceutical compositions of compounds of the invention either alone or in combination, in admixture with one or more pharmaceutically acceptable carriers.

In a further aspect, the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease wherein an inhibition of PDE4 activity along with muscarinic M3 receptor antagonism is desirable.

In particular the compounds of the invention alone or combined with other active ingredients may be administered for the prevention and/or treatment of a disease the respiratory tract characterized by airway obstruction such as asthma and COPD. In one embodiment, the compounds of the invention may be administered for the prevention and/or treatment of COPD.

In a further aspect, the present invention provides the use of compounds of the invention for the preparation of a medicament for the prevention and/or treatment of any disease wherein an inhibition of PDE4 activity along with muscarinic M3 receptor antagonism is desirable.

Moreover the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the present invention provides a suitable inhalation device, comprising a pharmaceutical composition of a compound of the invention, which may be respectively selected from a single- or multi-dose dry powder inhaler, a pressurized metered dosed inhaler or a nebulizer and in particular a soft mist nebulizer.

A further aspect of the present invention provides a kit comprising the pharmaceutical compositions of a compound of the invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" includes fluorine, chlorine, bromine, and iodine, preferably chlorine.

The term "$(C_1-C_x)$ alkyl" where x is an integer greater than 1, refers to straight and branched chain alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$alkylene" refers to a divalent $(C_1-C_x)$alkyl radical, wherein $(C_1-C_x)$alkyl is as above defined.

The term "$(C_1-C_x)$ alkoxy" where x is an integer greater than 1 refers to straight and branched chain alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expression "$(C_1-C_x)$haloalkyl" refers to the above defined "$(C_1-C_x)$alkyl" groups wherein one or more hydrogen atoms are replaced by one or more halogen atoms, which can be the same or different from each other.

Examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$ cycloalkyl" where y is an integer greater than or equal to 3, refers to saturated cyclic hydrocarbon groups containing from 3 to y ring carbon atoms. Examples include cyclopropyl, cyclobutyl, cyclopentyl, cyclohexyl, and cycloheptyl.

The expression "$(C_3-C_y)$cycloalkylcarbonyl" refers to $(C_3-C_y)$cycloalkylCO— groups wherein the group "$(C_3-C_y)$cycloalkyl" has the meaning above defined.

The term "$(C_2-C_6)$alkenyl" refers to straight or branched, conjugated or non-conjugated, carbon chains with one or more double bonds, in cis or trans configuration, wherein the number of atoms is in the range 2 to 6.

The term "$(C_5-C_z)$cycloalkenyl" where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number of atoms is in the range 2 to 6.

The term "aryl" refers to mono or bi-cyclic systems which have 6 to 10 ring carbon atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S or O).

Examples of suitable aryl or heteroaryl monocyclic systems with 5 to 6 ring atoms include, for instance, benzene (phenyl), thiophene (thiophenyl), pyrrole (pyrrolyl), pyrazole (pyrazolyl), imidazole (imidazolyl), triazole (triazolyl), tetrazole (tertrazolyl), isoxazole (isoxazolyl), oxazole (oxazolyl), isothiazole (isothiazolyl), thiazole (thiazolyl), pyridine (pyridinyl), furan (furanyl) derived radicals and the like.

Examples of suitable aryl or heteroaryl bicyclic systems with more than 6 ring atoms include naphthalene (naphthylenyl), biphenylene (biphenylenyl), tetrahydronaphthalene (tetrahydronaphthylenyl), purine (purinyl), pteridine (pteridinyl), benzimidazole (benzimidazolyl), benzotriazole (benzotriazolyl), quinoline (quinolinyl), isoquinoline (isoquinolinyl), indole (indolyl), isoindole (isoindolyl), indazole (indazolyl), benzothiophene (benzothiophenyl), benzofuran (benzofuranyl), benzoxazole (benzoxazolyl), dihydrobenzo dioxin, dihydrobenzo dioxepin, benzo-oxazin radicals and the like.

By analogy the expression "arylene" refers to divalent mono or bi-cyclic systems which have 6 to 10 ring carbon atoms, wherein at least one ring is aromatic. Non-limiting examples are phenylenediyl diradical at any suitable position.

The expression "heteroarylene" specifically "$(C_5-C_6)$ heteroarylene" refers to divalent monocyclic ring systems with 5 to 6 ring atoms, and in which at least one ring atom is a heteroatom (e.g. N, NH, S or O). Non-limiting examples of suitable $(C_5-C_6)$ heteroarylene systems include, for instance, thiophenediyl, furanediyl, pyrrolediyl, pyrazolediyl, imidazolediyl, triazolediyl, tetrazolediyl, isoxazolediyl, oxazolediyl, isothiazolediyl, thiazolediyl, pyridinediyl diradicals at any suitable position and the like.

The expression "heterocyclic ring system" refers to optionally substituted mono-, bi- or tri-cyclic ring systems which may be saturated partially unsaturated, such as heterocycloalkyl groups having 3 to 11 ring atoms or specifically $(C_3-C_7)$ heterocycloalkyl groups, in which at least one ring atom is a heteroatom (e.g. N, S or O), included in the definition are bridged mono-, bi- or tri-cyclic ring systems.

Examples of "heterocyclic ring system" are represented by: oxetan-yl, pyrrolidinyl, imidazolidinyl, piperazinyl, piperidinyl, quinuclidinyl, 8-azabicyclo[3.2.1]octanyl or dehydroxy scopine radical all optionally substituted by $(C_1-C_x)$ alkyl or benzyl on a nitrogen atom.

By analogy, the derived expression "heterocycloalkylene" refers to the above-defined heterocyclic ring systems, e.g. $(C_3-C_7)$ heterocycloalkylene divalent groups, when they are divalent groups bridging two parts of a molecule.

The present invention is directed to a class of compounds acting both as inhibitors of the phosphodiesterase 4 (PDE4) enzyme and as muscarinic M3 receptor antagonists.

The present invention relates to derivatives of general formula (I), N-oxides on the pyridine ring, deuterated derivatives and pharmaceutically acceptable salts or solvates thereof:

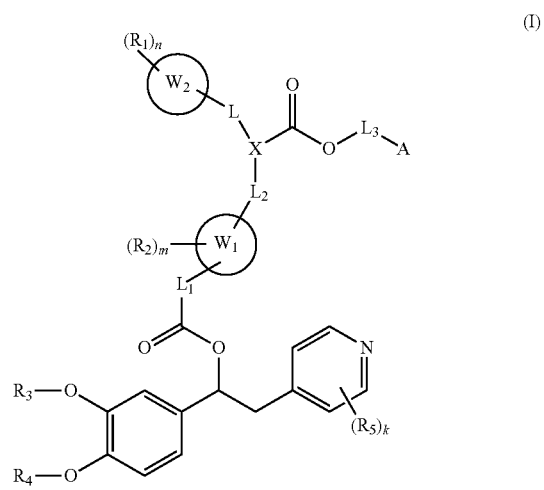

(I)

wherein $R_1$, $R_2$, $R_3$, $R_4$, $R_5$, L, $L_1$, $W_1$, $L_2$, $W_2$, X, $L_3$, A, n, m and k are as above defined.

Preferred compounds of formula (I) are those wherein the saturated heterocyclic ring system A is represented by a group of formula (i), or (iv):

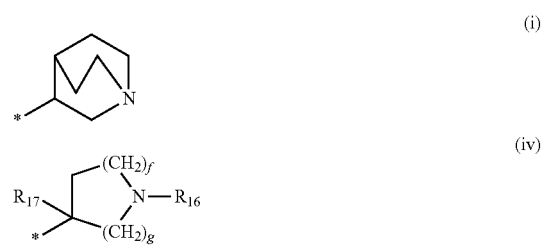

(i)

(iv)

wherein f=1; g=2; $R_{17}$ is hydrogen; $R_{16}$ is methyl and the asterisk (*) represents the point of attachment to $L_3$ in Formula (I).

It will be apparent to those skilled in the art that compounds of general formula (I) contain at least one stereogenic center, namely represented by the carbon atom (1) in formula (I)" below, and therefore exist as optical stereoisomers.

Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)", which are compounds of formula (I) as above defined where the absolute configuration of carbon (1) is that shown below:

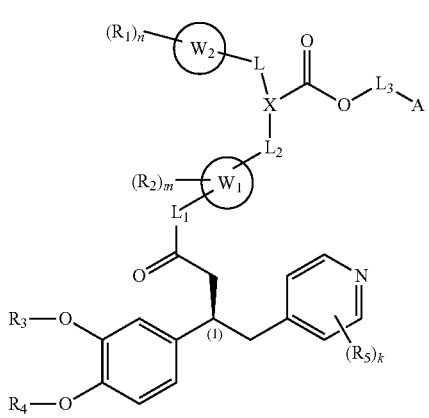

(I)″

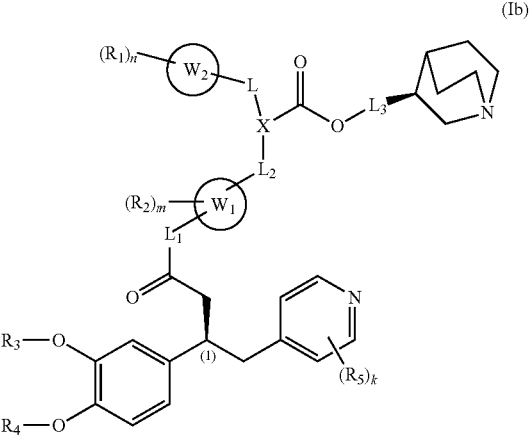

(Ib)

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

In one embodiment, when A is a group of formula (i) as above defined, or a group of formula (iv) or (v) containing a stereogenic carbon atom at the point of attachment of the group A to L3 in formula (I), compounds of formula (I) may exist as at least four diastereoisomers (Ia), (Ib), (Ic), and (Id), when A is (i); (Ie), (If), (Ig), and (Ih) when A is (iv) and (Ii), (Il), (Im), (In) when A is (v) as it is herebelow reported, which are comprised within the scope of the present invention. When X is the group $X_2$, or the groups $X_1$ and $X_3$ wherein i and i' are different from each other, each (Ia), (Ib), (Ic), (Id), (Ie), (If), (Ig), (Ih), (Ii), (Il), (Im), and (In) is constituted by a couple of corresponding epimers at the stereogenic center at the carbon atom of group X.

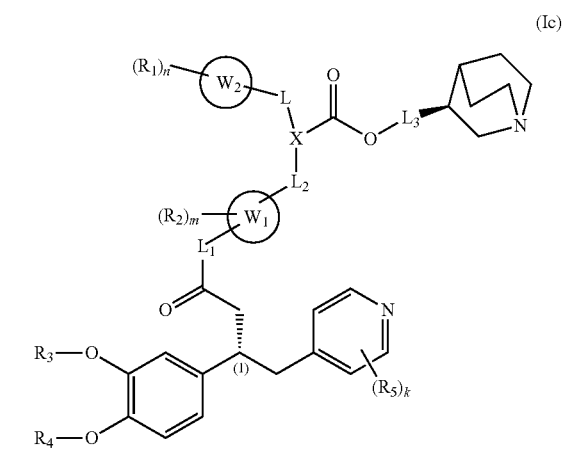

(Ic)

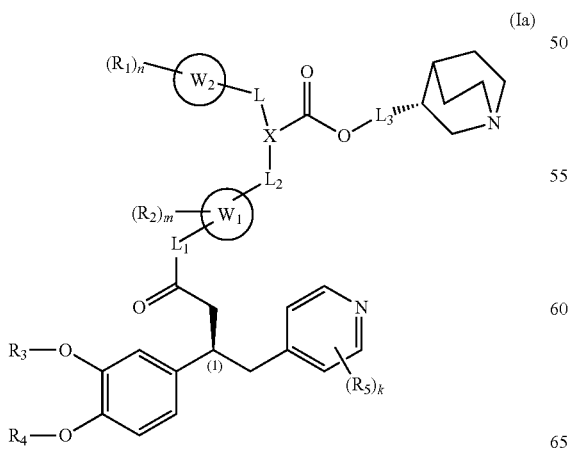

(Ia)

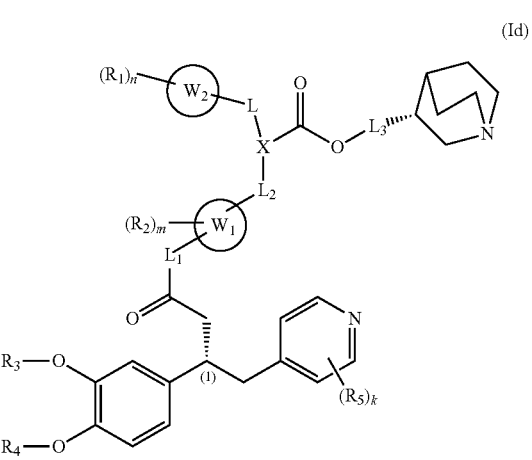

(Id)

(Ie)
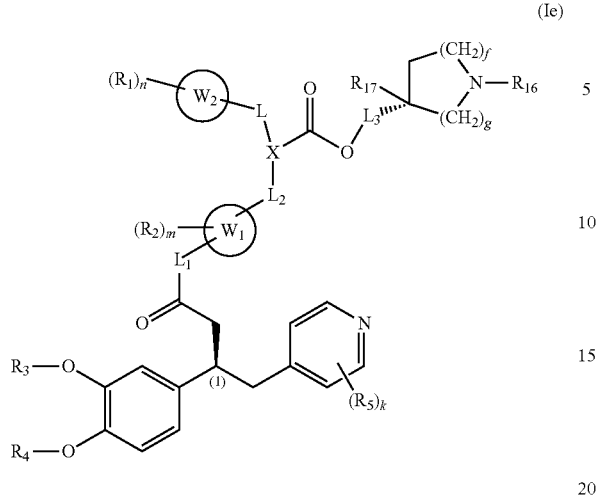
(Ih)
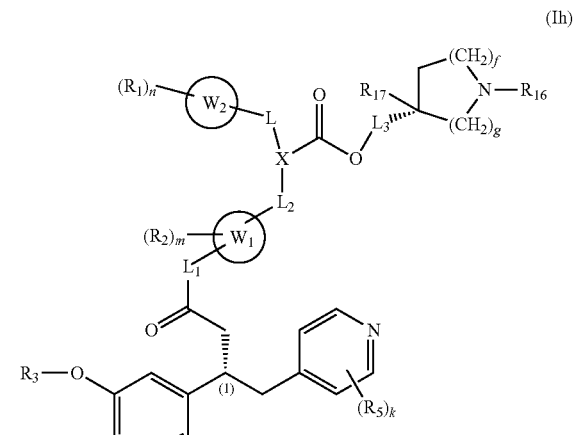
(If)
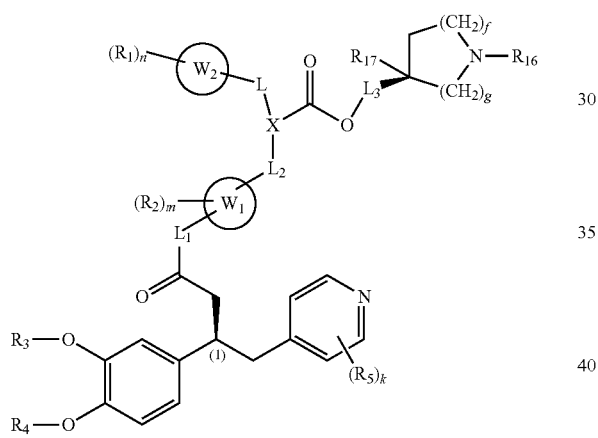
(Ii)
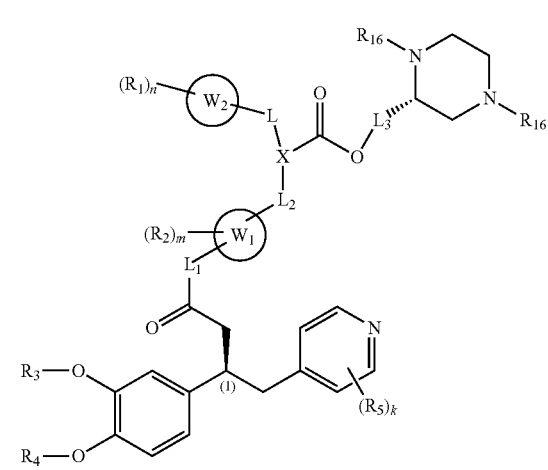
(Ig)
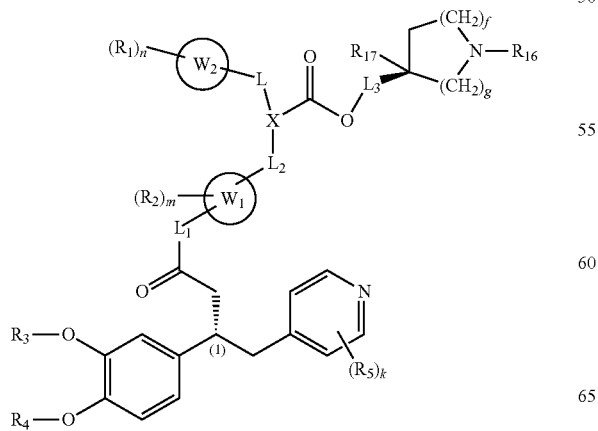
(Il)
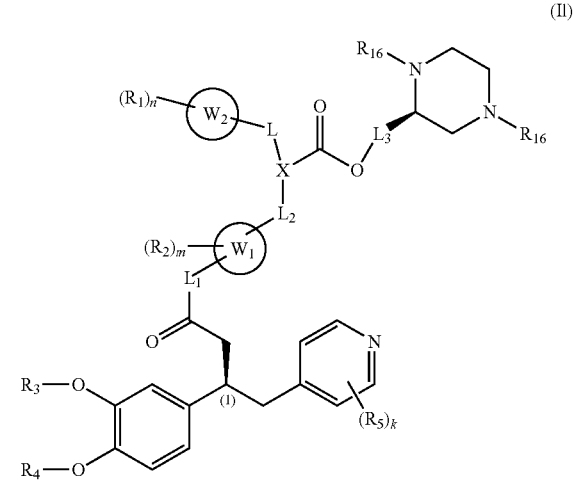

-continued

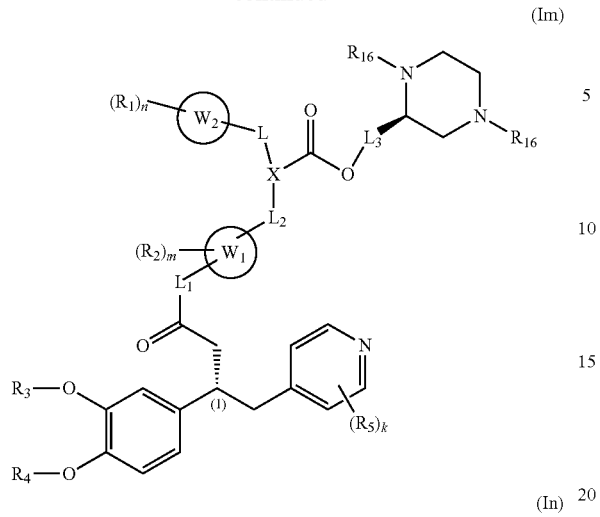
(Im)

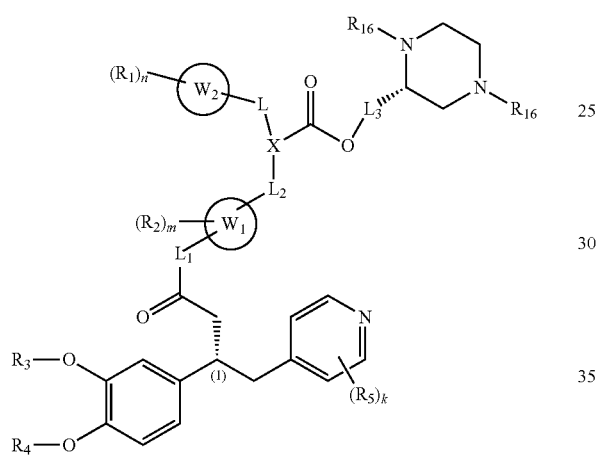
(In)

It will be apparent to the skilled person that compounds of formula (Ia), (Ib), (Ic), (Id), and (Ie), (If), (Ig), (Ih) (Ii), (Il), (Im) and (In) may be also obtained as single diastereoisomers wherein, when X contains a stereogenic centre at carbon atom, said stereogenic centre is defined as R or S.

In one embodiment, compounds of formula (Ia) or (Ie) are provided as above reported, or as single diastereoisomers thereof.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id), (Ie), (If), (Ig), (Ih), (Ii), (Il), (Im), (In), (I)' and (I)'' as well mutatis mutandis.

In a preferred embodiment, the present invention provides compounds of formula (IA), which are N-oxides on the pyridine ring of compounds of formula (I) wherein X is the group $X_2$ and i'' is 0, deuterated derivatives and pharmaceutically acceptable salts and solvates thereof:

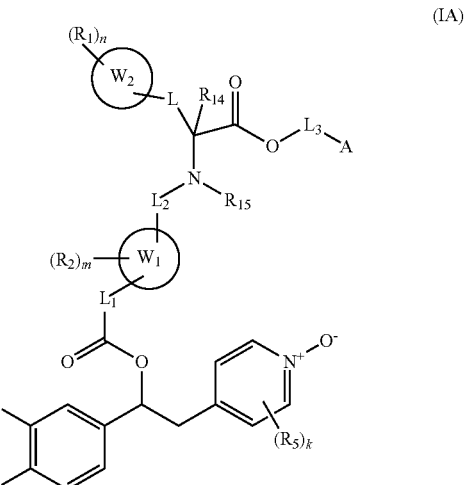
(IA)

wherein $R_1$, $R_2$, $R_3$, $R_4$, $R_5$, $R_{14}$, $R_{15}$, L, $L_1$, $W_1$, $L_2$, $W_2$, A, $L_3$, m, n, and k are as described above.

In another preferred embodiment the present invention provides compounds of formula (IB), which are N-oxides on the pyridine ring of compounds of formula (I) wherein L is a bond, X is the group $X_1$, deuterated derivatives and pharmaceutically acceptable salts and solvates thereof:

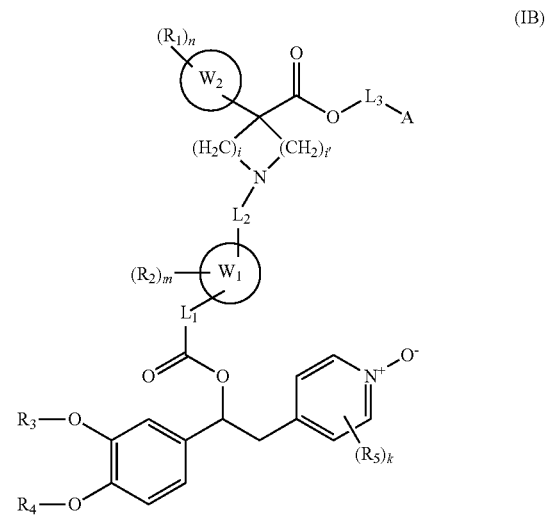
(IB)

wherein $R_1$, $R_2$, $R_3$, $R_4$, $R_5$, $L_1$, $W_1$, $L_2$, $W_2$, A, i, i', m, n, and k are as described for formula (I).

In a preferred embodiment of formula (IA) or (IB), k is 2 and $R_5$ are halogen atoms. In a further preferred embodiment, $R_5$ are two chlorine atoms at positions 3 and 5 of the pyridine ring.

In one preferred embodiment, $R_4$ is selected from a $(C_1$-$C_6)$ alkyl and $R_3$ is selected from $(C_3$-$C_7)$ cycloalkyl or $(C_1$-$C_6)$ alkyl which is optionally substituted by $(C_3$-$C_7)$ cycloalkyl.

In another preferred embodiment, $R_3$ is $(C_1$-$C_6)$ alkyl and $R_4$ is $(C_1$-$C_6)$ alkyl.

In another preferred embodiment, $R_3$ and $R_4$ are both methyl.

A preferred group of compounds of formula (I) is that wherein the 4-pyridinyl ring is substituted at positions 3 and 5 with two atoms of chlorine, according to the general formula (IC):

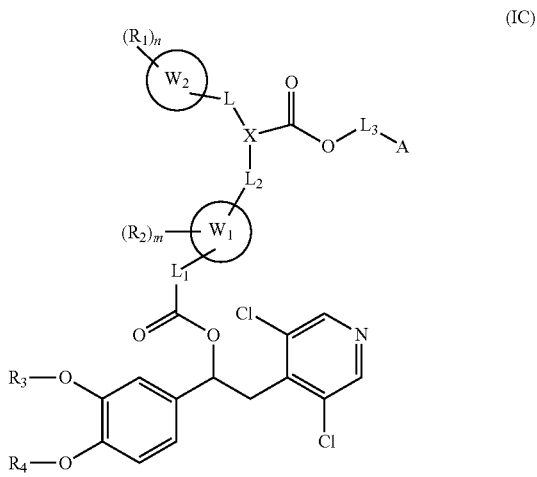

wherein $R_1$, $R_2$, $R_3$, $R_4$, A, L, $L_1$, $W_1$, $L_2$, $W_2$, X, $L_3$, m and n are as defined above for compounds of formula (I); and the corresponding N-oxide on the pyridine ring, deuterated derivatives and pharmaceutically acceptable salts and solvates thereof.

A more preferred group of compounds is that shown below according to general formula (ID):

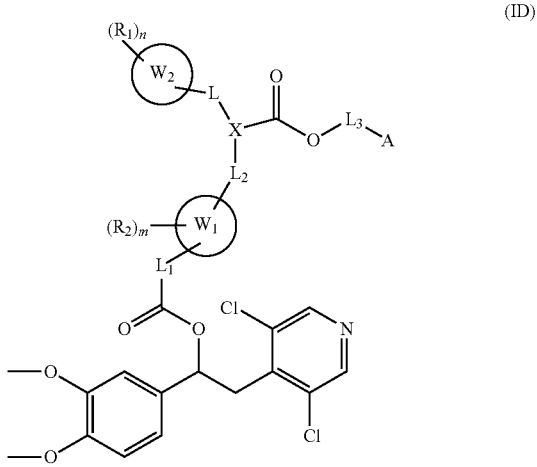

wherein $R_1$, $R_2$, A, L, $L_1$, $W_1$, $L_2$, $W_2$, X, $L_3$, m and n are as defined above for compounds of formula (I), the corresponding N-oxide on the pyridine ring, deuterated derivatives and pharmaceutically acceptable salts and solvates thereof In one embodiment of formula (ID) $L_1$ is a bond and $L_2$ and $L_3$ are both methylene.

In another embodiment of formula (ID) m is 0 and $W_1$ is phenylene-1,4-diyl or phenylene-1,3-diyl; alternatively named 1,4-phenylene, 1,3-phenylene.

In another embodiment of formula (ID) n is 0 and $W_2$ is unsubstituted phenyl.

In another embodiment of formula (ID) n is 1, $R_1$ is hydroxyl and $W_2$ is phenyl.

In another embodiment of formula (ID) X is a group of formula $X_1$ wherein both i and i' are 1 or 2, or a group of formula $X_2$ wherein i" is 0 and $R_{14}$ and $R_{15}$ are independently selected from H or methyl, or a group of formula $X_3$ wherein both i and i' are 1 and $R_{15}$ is H.

In another embodiment of formula (ID), A is a group of formula (i), or (iv):

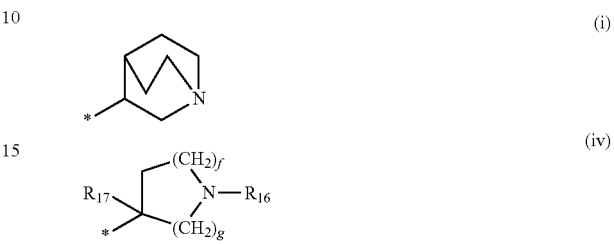

wherein f=1; g=2; $R_{17}$ is hydrogen; $R_{16}$ is methyl and the asterisk (*) represents the point of attachment to $L_3$ in Formula (I).

According to a preferred embodiment, the present invention provides the compounds reported below:

[(1S)-2-(3,5-dichloro-1-oxido-pyridin-1-ium-4-yl)-1-(3,4-dimethoxyphenyl)ethyl]3-[[[2-[(1-methyl-4-piperidyl)methoxy]-2-oxo-1-phenyl-ethyl]amino]methyl]benzoate;

[(1S)-2-(3,5-dichloro-1-oxido-pyridin-1-ium-4-yl)-1-(3,4-dimethoxyphenyl)ethyl]4-[[[2-[(1-methyl-4-piperidyl)methoxy]-2-oxo-1-phenyl-ethyl]amino]methyl]benzoate;

[(1S)-2-(3,5-dichloro-1-oxido-pyridin-1-ium-4-yl)-1-(3,4-dimethoxyphenyl)ethyl]4-[[[2-oxo-1-phenyl-2-[[(3S)-quinuclidin-3-yl]methoxy]ethyl]amino]methyl]benzoate;

Single diastereoisomer 1 of [(1S)-2-(3,5-dichloro-1-oxido-pyridin-1-ium-4-yl)-1-(3,4-dimethoxyphenyl)ethyl] 3-[[[2-[(1-methyl-4-piperidyl)methoxy]-2-oxo-1-phenyl-ethyl]amino]methyl]benzoate;

Single diastereoisomer 2 of [(1S)-2-(3,5-dichloro-1-oxido-pyridin-1-ium-4-yl)-1-(3,4-dimethoxyphenyl)ethyl] 3-[[[2-[(1-methyl-4-piperidyl)methoxy]-2-oxo-1-phenyl-ethyl]amino]methyl]benzoate;

Single diastereoisomer 1 of [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate;

Single diastereoisomer 2 of [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate;

Single diastereoisomer 1 of [(1S)-2-(3,5-dichloro-1-oxido-pyridin-1-ium-4-yl)-1-(3,4-dimethoxyphenyl)ethyl] 4-[[[2-oxo-1-phenyl-2-[[(3S)-quinuclidin-3-yl]methoxy]ethyl]amino]methyl]benzoate;

Single diastereoisomer 1 of [(1S)-2-(3,5-dichloro-1-oxido-pyridin-1-ium-4-yl)-1-(3,4-dimethoxyphenyl)ethyl] 4-[[[1-(3-hydroxyphenyl)-2-[(1-methyl-4-piperidyl)methoxy]-2-oxo-ethyl]amino]methyl]benzoate;

Single diastereoisomer 2 of [(1S)-2-(3,5-dichloro-1-oxido-pyridin-1-ium-4-yl)-1-(3,4-dimethoxyphenyl)ethyl] 4-[[[2-oxo-1-phenyl-2-[[(3S)-quinuclidin-3-yl]methoxy]ethyl]amino]methyl]benzoate;

Single diastereoisomer 2 of [(1S)-2-(3,5-dichloro-1-oxido-pyridin-1-ium-4-yl)-1-(3,4-dimethoxyphenyl)ethyl] 4-[[[1-(3-hydroxyphenyl)-2-[(1-methyl-4-piperidyl)methoxy]-2-oxo-ethyl]amino]methyl]benzoate.

The expression "single diastereoisomer" is reported near the chemical name of each compound of formula (I) isolated as single diastereoisomer whose absolute configuration at the stereogenic carbon atom of X was not determined.

The present invention also provides processes for the preparation of compounds of the invention.

Compounds of formula (IA) can be obtained according to general synthetic routes of Scheme A below reported or following slightly modified procedures that the skilled person can easily apply.

Processes of preparation described below and reported in the following Scheme A should not be viewed as limiting the scope of the synthetic methods available for the preparation of the compounds of the invention.

In the following Scheme A, for compounds of formula (IA) and for compounds of formula (II) to (IX), wherein X is $X_2$; unless otherwise indicated, $R_1$, $R_2$, $R_3$, $R_4$, $R_5$, $R_{14}$, L, $L_1$, $W_1$, $L_2$, $W_2$, A, n, m, k and $L_3$ are as above defined, whereas Y is a bond or $-(CH_2)_{q'}$, wherein q' is an integer ranging from 1 to 3.

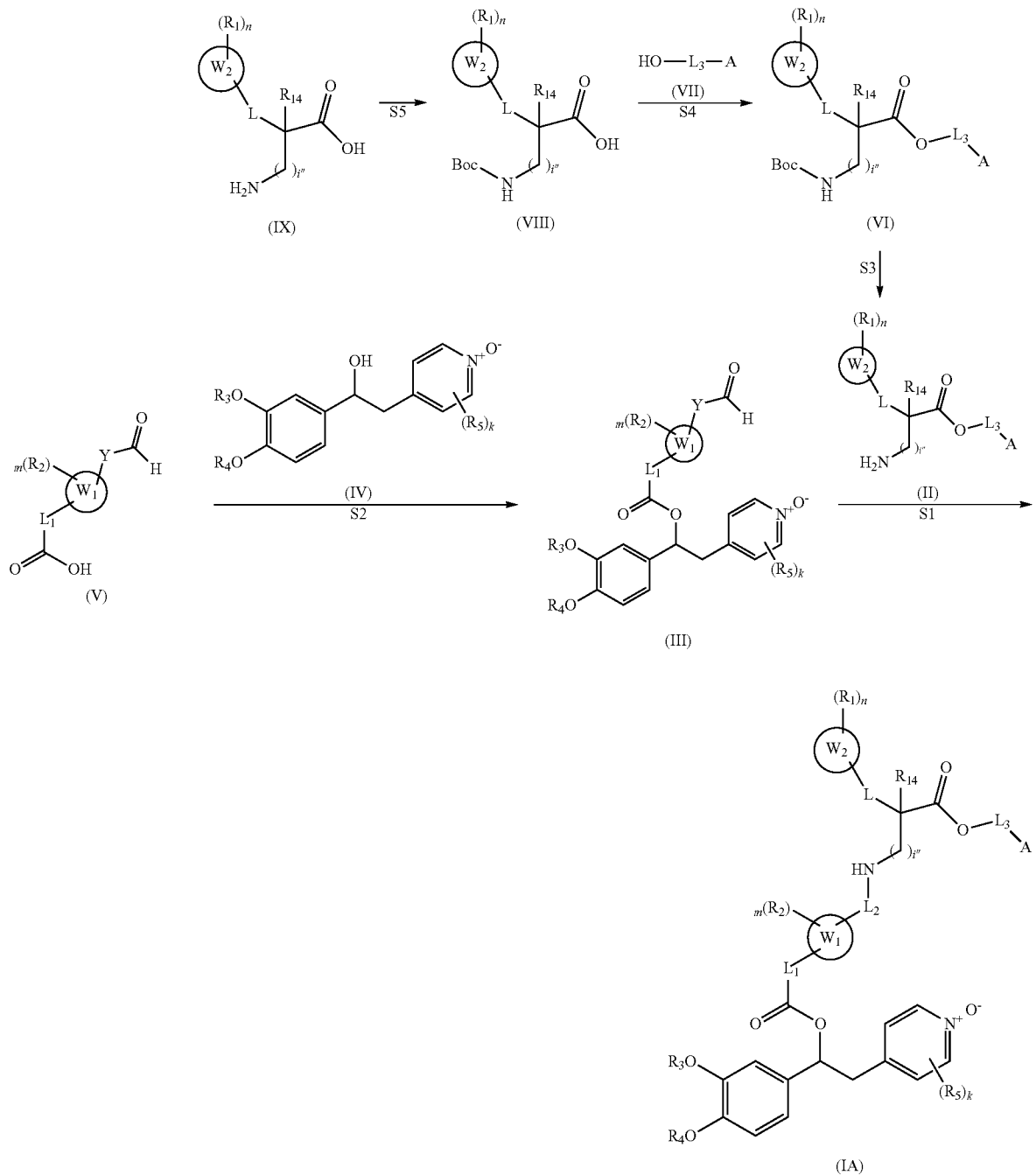

Scheme A

Compounds of formula (I) may be prepared according to Scheme 1/(S1) below by reaction of a compound of formula (III) with a compound of formula (II) as below reported.

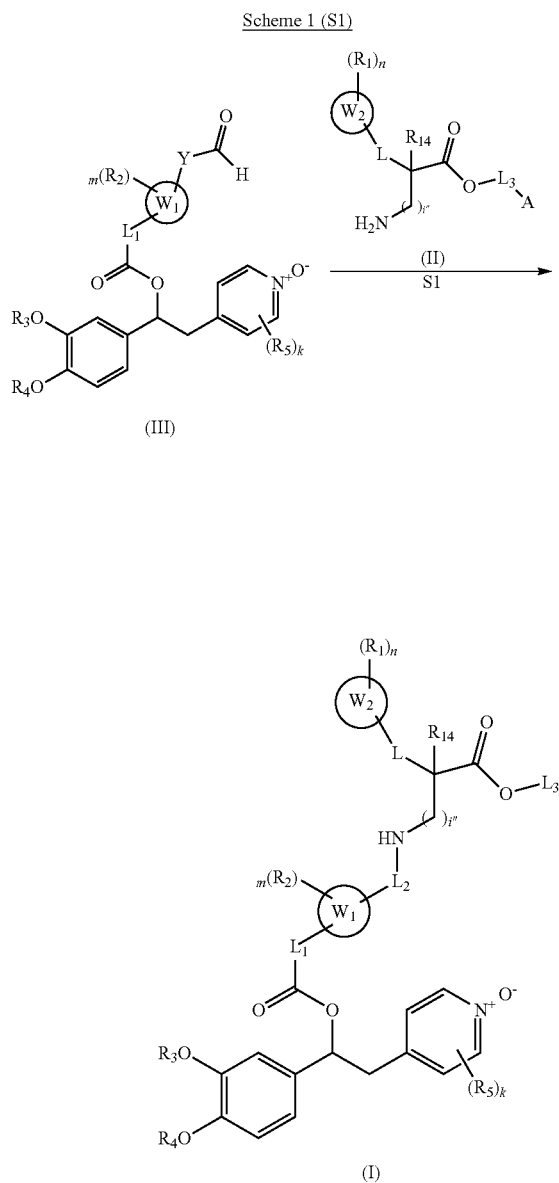

Typical reaction conditions comprise reacting a compound of formula (III) with a compound of formula (II) in a suitable solvent, such as acetonitrile, DCM, ethanol or pyridine in the presence of an optional acid, such as acetic acid, and an optional base, such as triethylamine, and a reducing agent, such as NaBH(OAc)$_3$ or NaBH$_3$CN, at an appropriate temperature, such as room (or ambient) temperature or 40° C. or 60° C.

Compounds of formula (III) may be prepared according to Scheme 2/(S2) below by reaction of a compound of formula (V) with a compound of formula (IV) as below reported.

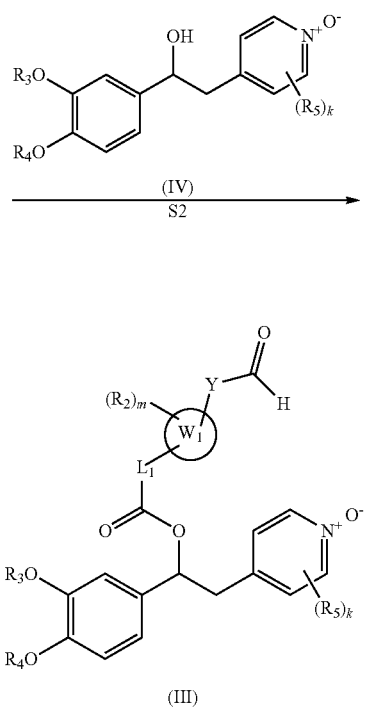

Typical reaction conditions comprise reacting a compound of formula (V) with a compound of formula (IV) in a suitable solvent, such as DCM, in the presence of a suitable coupling agent, such as EDC/DMAP or HATU, at an appropriate temperature, such as room (or ambient) temperature.

Compounds of formula (IV) may be prepared as described in the co-pending international application WO 2014/086849, which is incorporated herein by reference in its entirety, starting at page 42 scheme 8/A, and from page 58 for Intermediate 1/A, (S)-3,5-Dichloro-4-(2-(3,4-dimethoxyphenyl)-2-hydroxyethyl)pyridine 1-oxide, and the like where R$_3$ and R$_4$ are as above defined.

Compounds of formula (II) may be prepared according to Scheme 3/(S3) below by reaction of a compound of formula (VI) as below reported.

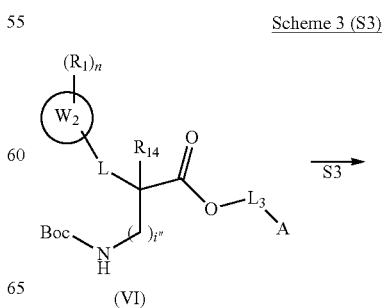

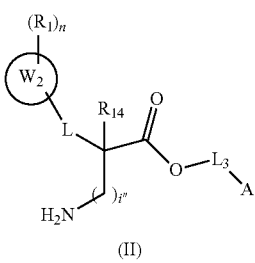

(II)

Typical reaction conditions comprise reacting a compound of formula (VI) in a suitable solvent, such as 1,4-dioxane, in the presence of a suitable acid, such as hydrochloric acid, at an appropriate temperature, such as room (or ambient) temperature.

Compounds of formula (VI) may be prepared according to Scheme 4/(S4) below by reaction of a compound of formula (VIII) with a compound of formula (VII) as below reported.

Scheme 4 (S4)

(VIII) → (VI)

Typical reaction conditions comprise reacting a compound of formula (VIII) with a compound of formula (VII) in a suitable solvent, such as THF in the presence of a suitable coupling agent, such as DCC/HOBt or EDC/DMAP or HATU, at an appropriate temperature, such as room (or ambient) temperature or 40° C.

Compounds of formula (VIII) may be prepared according to Scheme 5/(S5) below by reaction of a compound of formula (IX) as below reported.

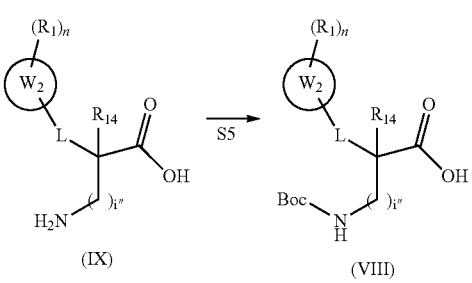

Scheme 5 (S5)

(IX) → (VIII)

Typical reaction conditions comprise reacting a compound of formula (IX) with di-tert-butyl dicarbonate, in a suitable solvent, such as 1,4-dioxane/water, in the presence of a suitable base such as sodium hydroxide, at an appropriate temperature, such as 0° C. or room (or ambient) temperature.

The processes described are particularly advantageous as they are susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups which may be present in the intermediate compounds and reactants depicted in Scheme A and which could generate unwanted side reactions and by-products, need to be properly protected before the relevant reaction takes place. Likewise, subsequent deprotection of those same protected groups may follow upon completion of the said reactions.

According to the present invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known (see, for a general reference, T. W. Green; Protective Groups in Organic Synthesis (Wiley, N.Y. 1999), which is incorporated herein by reference in its entirety).

Likewise, selective protection and deprotection of any of the said groups, for instance including carbonyl, hydroxy or amino groups, may be accomplished according to well-known methods commonly employed in organic synthetic chemistry.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates, and polyethylene glycols.

Formulations for vaginal administration may be in the form of cream, gel, paste, foam, or spray formula containing, in addition to the active ingredient, known suitable carriers.

For topical administration, the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds of the invention are preferably administered by inhalation.

Inhalable preparations include inhalable powders, propellant-containing metered aerosols or propellant-free inhalable formulations and may be administered through a suitable inhalation device which may be respectively selected from a dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic, or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention, with an antimuscarinic agent selected from the group consisting of aclidinium, tiotropium, ipratropium, trospium, glycopyrronium and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414 and RPL-554.

The present invention also provides combinations of a compound of the invention, with a P38 MAP kinase inhibitor selected from the group consisting of semapimod, talmapimod, pirfenidone, PH-797804, GSK-725, minokine and losmapimod and salts thereof.

In a preferred embodiment, the present invention provides combinations of a compound of the invention with an IKK2 inhibitor.

The present invention also provides combinations of a compound of the invention with a FINE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The present invention also provides combinations of a compound of the invention with a leukotriene modulator selected from the group consisting of montelukast, zafirlukast and pranlukast.

The present invention also provides combinations of a compound of the invention with a NSAID selected from the group consisting of ibuprofen and ketoprofen.

The present invention also provides combinations of a compound of the invention with a mucus regulator selected from the group consisting of INS-37217, diquafosol, sibenadet, CS-003, talnetant, DNK-333, MSI-1956 and gefitinib.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage of 0.001 to 1000 mg/day, preferably 0.1 to 500 mg/day.

When they are administered by inhalation route, the dosage of the compounds of the invention is advantageously 0.01 to 20 mg/day, preferably 0.1 to 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

The compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

Boc=tert-butoxycarbonyl;
DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy) methaniminium hexafluorophosphate;
EDC=1-ethyl-3-(3-dimethylaminopropyl) carbodiimide hydrochloride;
DBU=1,8-diazabicyclo[5.4.0]undec-7-ene;
DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
NMR=nuclear magnetic resonance;
HPLC=high pressure liquid chromatography;
MPLC=medium pressure liquid chromatography;
FC=supercritical fluid chromatography
General Experimental Details
Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2

LC-MS was performed on a Waters 2795 Alliance HT HPLC with Waters 2996 Diode Array Detector coupled to a Micromass ZQ, single quadrapole mass spectrometer using a Waters Xterra MS C18 column (5 µm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
Method 3

UPLC-MS was performed on a Waters Acquity I-Class with Waters Diode Array Detector coupled to a Waters SQD2 single quadrapole mass spectrometer using an Waters HSS C18 column (1.8 µm, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).
Method 4

UPLC-MS was performed on a Waters Acquity I-Class with Waters Diode Array Detector coupled to a Waters SQD2 single quadrapole mass spectrometer using an Waters BEH Shield RP18 column (1.7 µm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).
Supercritical Fluid Chromatography—Mass Spectrometry
Analytical Conditions
Method 5

SFC-MS was performed on a Waters/Thar SFC systems with Waters SQD using a Lux Cellulose-C column with a 15% methyl alcohol/$CO_2$ (with 0.1% diethylamine) isocratic run at 5 mL/min, 120 bar backpressure, 40° C. column temperature.
Method 6

SFC-MS was performed on a Waters/Thar SFC systems with Waters SQD using a YMC Amylose-C column with a 40% iso-propyl alcohol/$CO_2$ (with 0.1% diethylamine) isocratic run at 5 mL/min, 120 bar backpressure, 40° C. column temperature.

Method 7

SFC-MS was performed on a Waters/Thar SFC systems with Waters SQD using a YMC Amylose-C column with a 55% iso-propyl alcohol/$CO_2$ (with 0.1% diethylamine) isocratic run at 5 mL/min, 120 bar backpressure, 40° C. column temperature.

NMR $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under API conditions. Collected fractions were analysed by LCMS (Waters Acquity systems with Waters SQD).

Chiral Separation Protocol

The diastereomeric separation of compounds was achieved either by chiral High Performance Liquid Chromatography (HPLC) using a Gilson Trilution preparative HPLC system (322 pump, 155 UV/VIS, GX281 liquid handler and fraction collector) or by Supercritical Fluid Chromatography (SFC) using a Waters Thar Prep100 preparative SFC system (P200 $CO_2$ pump, 2545 modifier pump, 2998 UV/VIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, a Phenomenex Lux Cellulose-4, an YMC Amylose-C or an YMC Cellulose-C at 5 μm 250×20–21.2 mm ID.

Appropriate isocratic methods were selected based on methanol, ethanol or isopropanol solvent systems under un-modified or basic conditions.

The standard SFC method used was modifier, $CO_2$, 100 mL/min, 120 Bar backpressure, 40° C. column temperature. The standard HPLC method used was modifier, heptane, 5 mL/min and room temperature.

The modifier used under basic conditions was diethylamine (0.1% V/V). The modifier used under acidic conditions was either formic acid (0.1% V/V) or trifluoroacetic acid (0.1% V/V).

The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

HPLC purification was controlled by Gilson Trilution software monitoring two wavelengths and triggered at a threshold collection value, typically 260 nm. Collected fractions were analyzed by HPLC (Agilent 1200 series HPLC system). The fractions that contained the desired product were concentrated by vacuum centrifugation.

Compounds Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Many of the compounds described in the following Examples have been prepared from stereochemically pure starting materials, for example 95% enantiomeric excess (ee).

The stereochemistry of the compounds in the Examples, where indicated, has been assigned on the assumption that absolute configuration at resolved stereogenic centers of staring materials is maintained throughout any subsequent reaction conditions.

Compounds isolated as single diastereoisomers whose absolute configuration at a stereogenic center in general formula (I) or (I') and (I''), further to stereogenic centre (1), was not determined, are herebelow referred to as Single Diastereoisomers without mention in their chemical name of absolute configuration for the unknown stereogenic center.

Intermediate 1

[(1S)-2-(3,5-dichloro-1-oxido-pyridin-1-ium-4-yl)-1-(3,4-dimethoxyphenyl)ethyl] 3-formylbenzoate

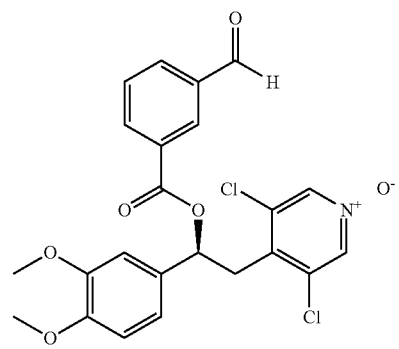

A solution of (1S)-2-(3,5-dichloro-1-oxido-pyridin-1-ium-4-yl)-1-(3,4-dimethoxyphenyl)ethanol, obtained as described in the co-pending international application WO 2014/086849, which is incorporated herein by reference in its entirety, page 58, (688 mg, 2 mmol), 3-formylbenzoic acid (300 mg, 2 mmol), N-(3-dimethylaminopropyl)-N'-ethylcarbodiimide hydrochloride (767 mg, 4 mmol) and 4-dimethylaminopyridine (122 mg, 1 mmol) in anhydrous DCM (30 mL) was stirred at room temperature for 21 hours. The reaction mixture was partitioned between saturated aqueous NaHCO$_3$ solution (20 mL) and DCM (10 mL) and filtered through a phase separator cartridge. The cartridge was washed thoroughly with DCM and the solvent was removed in vacuo. The crude material was purified by silica gel column chromatography eluting with 50% EtOAc in DCM to afford the title compound as an off-white solid (863 mg, 91%).

$^1$H NMR (400 MHz, CDCl$_3$): δ 10.08 (s, 1H), 8.54 (t, J=1.7 Hz, 1H), 8.27 (dt, J=7.8, 1.5 Hz, 1H), 8.14 (s, 2H), 8.09 (dt, J=7.7, 1.5 Hz, 1H), 7.63 (t, J=7.7 Hz, 1H), 7.05 (dd, J=8.2, 2.1 Hz, 1H), 7.00 (d, J=2.1 Hz, 1H), 6.87 (d, J=8.3 Hz, 1H), 6.33 (dd, J=9.7, 4.6 Hz, 1H), 3.92 (s, 3H), 3.88 (s, 3H), 3.76 (dd, J=14.0, 9.8 Hz, 1H), 3.39 (dd, J=14.0, 4.6 Hz, 1H). LCMS (Method 1): [MH+]=476 at 3.55 min.

The following intermediate was synthesized via the same procedure.

Et$_2$O (4.3 mL, 8.56 mmol) was added dropwise over a period of 10 minutes. The mixture was stirred in an ice bath for one hour then allowed to warm to room temperature and stirred for 72 hours. The mixture was cooled in an ice-bath and a 1 N aqueous solution of NaOH (1 mL) was added dropwise over a period of 10 minutes followed by water (0.5 mL). The mixture was stirred at room temperature for one hour, and then filtered through a Celite® cartridge which was then washed through with a small amount of THF and water. The combined filtrates were concentrated in vacuo to give a racemic mixture of the title product as a colourless oil (792 mg, 76%). LCMS (Method 2): [MH+]=142 at 0.60 min.

Purification of the Mixture of Enantiomers by Chiral Preparative SFC Afforded the Single Enantiomers.

Title compound (Intermediate 3, single enantiomer 1) was obtained as a light brown gum (235 mg, 59%). LCMS (Method 4): [MH+]=142 at 0.62 min. Chiral analysis (Method 5) at 9.56 min. [α]$_D^{20}$=−51.17° (c=0.3 g/100 mL, CH$_3$OH).

Title compound (Intermediate 4, single enantiomer 2) was obtained as a light brown gum (203 mg, 51%). LCMS (Method 4): [MH+]=142 at 0.61 min. Chiral analysis (Method 5) at 11.28 min. [α]$_D^{20}$=+36.33° (c=0.3 g/100 mL, CH$_3$OH).

| Structure | Intermediate number | Analytical Data |
|---|---|---|
| 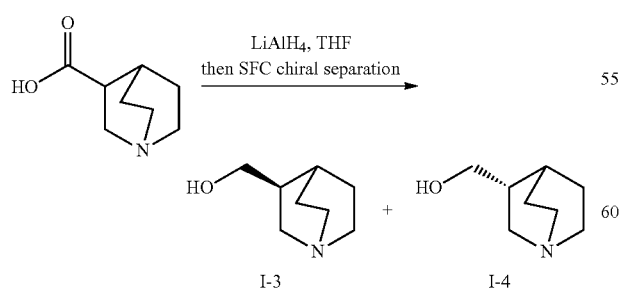 | Intermediate 2 | LCMS (Method 1): [MH+] = 476 at 3.65 min. |

Intermediate 3 and Intermediate 4

[(3S)-quinuclidin-3-yl]methanol (I-3) and [(3R)-quinuclidin-3-yl]methanol (I-4)

Intermediate 5

(1-Methyl-4-piperidyl)methyl 2-(tert-butoxycarbonylamino)-2-phenyl-acetate

A solution of quinuclidine-3-carboxylic acid (665 mg, 4.28 mmol) in dry THF (7 mL) was stirred under N$_2$ and cooled in an ice-water bath. A 2 M solution of LiAlH$_4$ in A mixture of 2-((tert-butoxycarbonyl)amino)-2-phenylacetic acid (1.0 g, 3.98 mmol), N,N'-dicyclohexylcarbodiimide (1.64 g, 7.97 mmol) and 1-hydroxybenzotriazole hydrate (1.08 g, 7.97 mmol) in THF (25 mL) was stirred at room temperature. After one hour, a solution of (1-methyl-4-piperidyl)methanol (0.62 g, 4.78 mmol) was added and the mixture was stirred at room temperature for 24 hours. The reaction mixture was filtered through a pad of Celite® and concentrated in vacuo. The residue was taken up into EtOAc (30 mL) and washed with saturated aqueous NaHCO₃ solution (2×40 mL), then with brine (40 mL). The organic phase was collected, filtered through a phase separator and the solvent was removed in vacuo to give the title compound as a pink gum (1.96 g, Theoretical yield=1.44 g).

LCMS (Method 1): [MH+]=363 at 2.54 min.

The following intermediates were synthesized via the same procedure.

| Structure | Intermediate number | Precursor | Analytical Data |
|---|---|---|---|
| 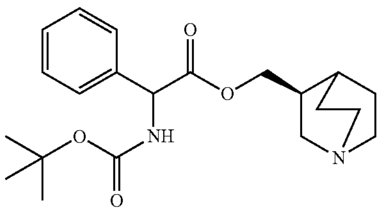 [SMILES: CC(C)(C)OC(=O)NC(C(=O)OC[C@@H]1CN2CCC1CC2)c1ccccc1] | Intermediate 6 | 2-((tert-butoxycarbonyl)amino)-2-phenylacetic acid and Intermediate 3 | LCMS (Method 4): [MH+] = 375 at 3.06 min. |
| 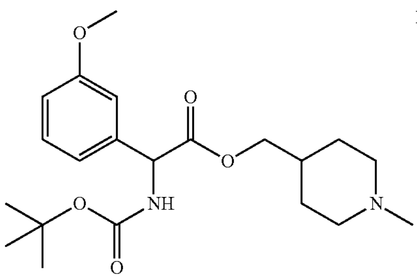 [SMILES: COc1cccc(C(NC(=O)OC(C)(C)C)C(=O)OCC2CCN(C)CC2)c1] | Intermediate 7 | 2-((tert-butoxycarbonyl)amino)-2-(3-methoxyphenyl)-acetic acid and (1-methyl-4-piperidyl)-methanol | LCMS (Method 4): [MH+] = 393 at 3.20 min. |

Intermediate 8

(1-Methyl-4-piperidyl)methyl 2-amino-2-phenyl-acetate bis-hydrochloride

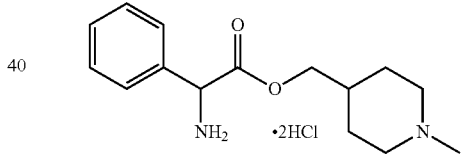

A solution of (1-methyl-4-piperidyl)methyl 2-(tert-butoxycarbonylamino)-2-phenyl-acetate (1.44 g, 3.98 mmol) in a 4 N solution of HCl in dioxane (7.0 mL, 28.0 mmol) was left standing at room temperature overnight. The solvent was removed by evaporation under reduced pressure, co-evaporated with diethyl ether, and dried in vacuo to give the title compound as an off-white solid (1.30 g, quantitative yield).

LCMS (Method 2): [MH+]=263 at 1.89 min.

The following intermediate was synthesized via the same method.

| Structure | Intermediate number | Precursor | Analytical Data |
|---|---|---|---|
| 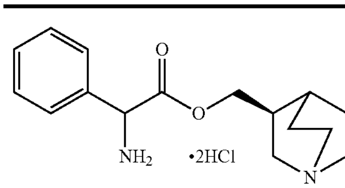 | Intermediate 9 | Intermediate 6 | LCMS (Method 4): [MH+] = 275 at 2.35 min |

Intermediate 10

(1-Methyl-4-piperidyl)methyl 2-amino-2-(3-hydroxyphenyl)acetate bis hydrobromide

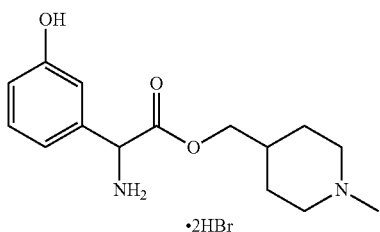 [SMILES: CN1CCC(COC(=O)C(N)c2cccc(O)c2)CC1]

·2HBr

To a solution of (1-methyl-4-piperidyl)methyl 2-(tert-butyloxycarbonylamino)-2-(3-methoxyphenyl)acetate (1.4 g, 3.6 mmol) in dry DCM (30 mL) at −78° C. was added a 1 N solution of boron tribromide in DCM (18 mL, 18 mmol). The reaction mixture was allowed to warm to room temperature and was stirred for 4 hours. After cooling the mixture back to −78° C., methanol (30 mL) was cautiously added. The reaction mixture was then warmed to room temperature and concentrated in vacuo to give the title compound as a brown foam (1.3 g, 82%) which was used in the next step without further purification.

LCMS (Method 2): [MH+]=279 at 1.33 min.

Example 1

[(1S)-2-(3,5-dichloro-1-oxido-pyridin-1-ium-4-yl)-1-(3,4-dimethoxyphenyl)ethyl] 3-[[[2-[(1-methyl-4-piperidyl)methoxy]-2-oxo-1-phenyl-ethyl]amino]methyl]benzoate

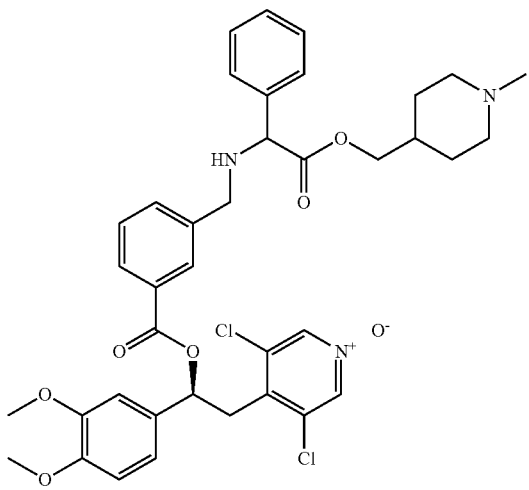

To a solution of [(1S)-2-(3,5-dichloro-1-oxido-pyridin-1-ium-4-yl)-1-(3,4-dimethoxyphenyl)ethyl] 3-formylbenzoate (Intermediate 1, 0.22 g, 0.46 mmol) and (1-methyl-4-piperidyl)methyl 2-amino-2-phenyl-acetate bis-hydrochloride Intermediate 8, (0.5 g, 1.5 mmol) in DCM (8 mL) was added Et$_3$N (0.48 mL, 3.0 mmol) and acetic acid (60 μL, 1.0 mmol). The mixture was stirred at room temperature for 24 hours. NaBH(OAc)$_3$ (0.24 g, 1.15 mmol) was then added and the solution was stirred for 24 hours. The reaction mixture was poured into saturated aqueous NaHCO$_3$ solution (10 mL), the phases were separated and the organic phase was further washed with saturated aqueous NaHCO$_3$ solution (2×15 mL). The organic phases were combined, and extracted with 1M HCl (2×20 mL), and combined acidic aqueous extracts were basified with excess NaHCO3 and extracted with EtOAc (3×20 mL). The organic extracts were combined, filtered through a phase separator and concentrated in vacuo. Purification of the crude material by preparative HPLC afforded the title compound (71 mg, 21%) as a white solid.

$^1$H NMR (400 MHz, CD$_3$CN): δ 8.17 (s, 2H), 8.03 (s, 1H), 7.94 (d, J=7.6 Hz, 1H), 7.57 (d, J=7.3 Hz, 1H), 7.47-7.33 (m, 6H), 7.10-7.04 (m, 2H), 6.95 (dd, J=1.5, 8.3 Hz, 1H), 6.26 (dd, J=4.4, 9.5 Hz, 1H), 4.39 (d, J=9.3 Hz, 1H), 3.92 (d, J=5.8 Hz, 2H), 3.83 (s, 3H), 3.82 (s, 3H), 3.79 (d, J=3.7 Hz, 2H), 3.75-3.68 (m, 1H), 3.41-3.34 (m, 1H), 2.75-2.53 (m, 3H), 2.15 (s, 3H), 1.83-1.75 (m, 2H), 1.52-1.45 (m, 3H), 1.23-1.11 (m, 2H). LCMS (Method 1): [MH+]=722 at 2.39 min.

The following compound was synthesized via a similar method as mixture of diastereoisomers.

| Structure | Example Number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate 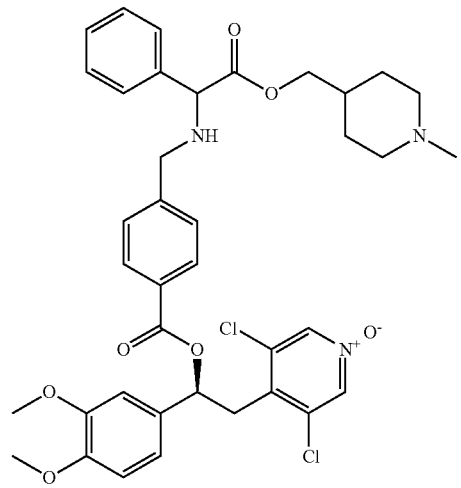 | Example 2 | Intermediate 2 and Intermediate 8 | ¹H NMR (400 MHz, CD₃CN): δ 8.17 (s, 2 H), 8.00 (d, J = 8.1 Hz, 2 H), 7.45 (d, J = 8.0 Hz, 2 H), 7.43-7.31 (m, 5 H), 7.10-7.03 (m, 2 H), 6.94 (d, J = 8.1 Hz, 1 H), 6.25 (dd, J = 4.7, 9.5 Hz, 1 H), 4.38 (s, 1 H), 3.92 (d, J = 6.1 Hz, 2 H), 3.84-3.77 (m, 9 H), 3.37 (dd, J = 4.5, 14.1 Hz, 1 H), 2.74-2.71 (m, 3 H), 2.14 (s, 3 H), 1.83-1.75 (m, 2 H), 1.53-1.45 (m, 3 H), 1.23-1.12 (m, 2 H). LCMS (Method 1): [MH+] = 722 at 2.44 min. |

Example 3

[(1S)-2-(3,5-dichloro-1-oxido-pyridin-1-ium-4-yl)-1-(3,4-dimethoxyphenyl)-ethyl] 4-[[[2-oxo-1-phenyl-2-[[(3S)-quinuclidin-3-yl]methoxy]ethyl]amino]methyl]-benzoate

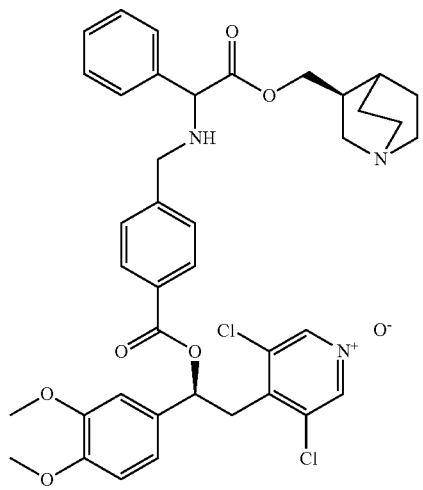

A mixture of [(1S)-2-(3,5-dichloro-1-oxido-pyridin-1-ium-4-yl)-1-(3,4-dimethoxyphenyl)ethyl] 4-formylbenzoate (Intermediate 2, 285 mg, 0.6 mmol), [(3S)-quinuclidin-3-yl] methyl 2-amino-2-phenyl-acetate bis hydrochloride (Intermediate 9, 246 mg, 0.71 mmol) and NaBH₃CN (38 mg, 0.6 mmol) in EtOH (5 mL) was stirred at room temperature for 18 hours. Additional [(1S)-2-(3,5-dichloro-1-oxido-pyridin-1-ium-4-yl)-1-(3,4-dimethoxyphenyl)ethyl] 4-formylbenzoate (100 mg, 0.2 mmol) and NaBH₃CN (10 mg, 0.16 mmol) were added and the mixture was stirred at room temperature for 24 hours. The solvent was removed in vacuo and the residue was suspended in EtOAc (25 mL) and extracted with 1N HCl (25 mL). The aqueous phase was washed further with EtOAc (25 mL) then basified with solid NaHCO₃ and extracted with EtOAc (2×25 mL).

The organic phases were combined, filtered through a phase separator and concentrated in vacuo. Purification of the crude material by preparative HPLC afforded the title compound (120 mg, 27%) as an off-white solid.

¹H NMR (400 MHz, CD₃CN): δ 8.19 (s, 2H), 8.02 (d, J=8.3 Hz, 2H), 7.45 (d, J=7.8 Hz, 2H), 7.42-7.36 (m, 5H), 7.11-7.04 (m, 2H), 6.95 (d, J=8.3 Hz, 1H), 6.26 (dd, J=4.5, 9.6 Hz, 1H), 4.37 (s, 1H), 4.12-4.01 (m, 2H), 3.85 (s, 3H), 3.83 (s, 3H), 3.81-3.78 (m, 2H), 3.76-3.68 (m, 1H), 3.38 (dd, J=4.3, 14.1 Hz, 1H), 2.86-2.79 (m, 1H), 2.73-2.63 (m, 5H), 2.30-2.15 (m, 1H), 1.89-1.83 (m, 1H), 1.56-1.49 (m, 3H), 1.43-1.38 (m, 1H), 1.31-1.25 (m, 1H). LCMS (Method 3): [MH+]=734 at 2.55 min.

Example 4 and Example 5

Single diastereoisomers of [(1S)-2-(3,5-dichloro-1-oxido-pyridin-1-ium-4-yl)-1-(3,4-dimethoxyphenyl)ethyl] 3-[[[2-[(1-methyl-4-piperidyl)-methoxy]-2-oxo-1-phenyl-ethyl]amino]methyl]benzoate (diastereoisomers 1 and 2)

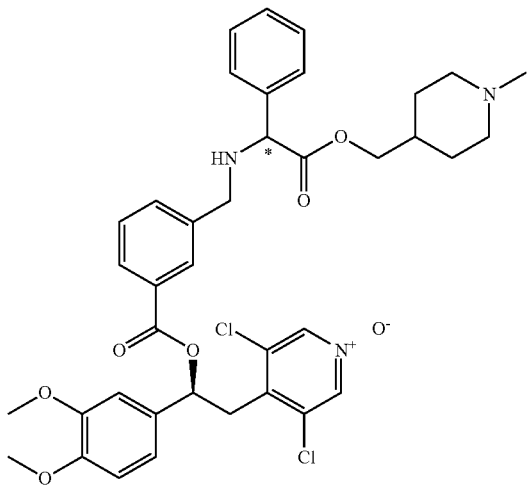

Purification of the mixture of diastereoisomers of Example 1 by chiral preparative SFC afforded the single diastereoisomers.

Title compound (Example 4, single diastereoisomer 1) was obtained as a white solid (24 mg, 7%).

$^1$H NMR (400 MHz, CD$_3$CN): δ 8.16 (s, 2H), 8.02 (s, 1H), 7.94 (d, J=7.6 Hz, 1H), 7.57 (d, J=7.6 Hz, 1H), 7.47-7.33 (m, 6H), 7.10-7.04 (m, 2H), 6.95 (d, J=8.3 Hz, 1H), 6.25 (dd, J=4.4, 9.7 Hz, 1H), 4.37 (s, 1H), 3.92 (d, J=6.1 Hz, 2H), 3.83 (s, 3H), 3.82 (s, 3H), 3.78 (s, 2H), 3.75-3.59 (m, 1H), 3.37 (dd, J=4.5, 14.1 Hz, 1H), 2.74-2.70 (m, 2H), 2.13 (s, 3H), 1.81-1.73 (m, 2H), 1.51-1.44 (m, 3H), 1.21-1.11 (m, 2H) NH not visible. LCMS (Method 1): [MH+]=722 at 2.41 min.

Chiral analysis (Method 6) at 3.26 min.

Title compound (Example 5, single diastereoisomer 2) was obtained as a white solid (25 mg, 8%).

$^1$H NMR (400 MHz, CD$_3$CN): δ 8.17 (s, 2H), 8.03 (s, 1H), 7.94 (d, J=7.8 Hz, 1H), 7.57 (d, J=7.8 Hz, 1H), 7.47-7.33 (m, 6H), 7.10-7.03 (m, 2H), 6.95 (d, J=8.3 Hz, 1H), 6.26 (dd, J=4.8, 9.6 Hz, 1H), 4.40 (s, 1H), 3.92 (d, J=6.1 Hz, 2H), 3.83 (s, 3H), 3.82 (s, 3H), 3.79 (d, J=4.7 Hz, 2H), 3.72 (tt, J=6.7, 6.6 Hz, 1H), 3.38 (dd, J=4.5, 14.1 Hz, 1H), 2.72 (d, J=11.6 Hz, 2H), 2.14 (s, 3H), 1.82-1.73 (m, 2H), 1.53-1.45 (m, 3H), 1.22-1.11 (m, 2H). NH not visible LCMS (Method 1): [MH+]=722 at 2.41 min. Chiral analysis (Method 6) at 4.07 min.

Compounds reported in the table herebelow were obtained as single diastereoisomers according to the procedure described in Examples 4 and 5 by chiral preparative SFC or chiral preparative HPLC.

| Structure | Reference | Precursor | Analytical Data |
| --- | --- | --- | --- |
| [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]-methyl]benzoate | Example 6 (diastereoisomer 1) | Example 2 | $^1$H NMR (400 MHz, CD$_3$CN): δ 8.18 (s, 2 H), 8.01 J = 8.3 Hz, 2 H), 7.45 (d, J = 8.6 Hz, 2 H), 7.43-7.33 (m, 5 H), 7.10-7.04 (m, 2 H), 6.95 (d, J = 8.3 Hz, 1 H), 6.26 (dd, J = 4.7, 9.5 Hz, 1 H), 4.38 (s, 1 H), 3.92 (d, J = 6.1 Hz, 2 H), 3.84 (s, 3 H), 3.82 (s, 3 H), 3.79 (d, J = 3.2 Hz, 2 H), 3.72 (dd, J = 12.0, 16.1 Hz, 1 H), 3.38 (dd, J = 4.5, 14.1 Hz, 1 H), 2.73 (d, J = 11.9 Hz, 2 H), 2.63 (s, 1 H), 2.11 (s, 3 H), 1.83-1.75 (m, 2 H), 1.54-1.46 (m, 3 H), 1.22-1.11 (m, 2 H). LCMS (Method 2): [MH+] = 722 at 3.1 min. Chiral analysis (Method 7) at 2.78 min. |
| [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]aminolmethyl]benzoate | Example 7 (diastereoisomer 2) | Example 2 | $^1$H NMR (400 MHz, CD$_3$CN): δ 8.18 (s, 2 H), 8.01 (d, J = 8.3 Hz, 2 H), 7.45 (d, J = 8.2 Hz, 2 H), 7.43-7.32 (m, 5 H), 7.10-7.04 (m, 2 H), 6.95 (d, J = 8.5 Hz, 1 H), 6.26 (dd, J = 4.6, 9.7 Hz, 1 H), 4.38 (s, 1 H), 3.92 (d, J = |

| Structure | Reference | Precursor | Analytical Data |
|---|---|---|---|
| | | | 6.1 Hz, 2 H), 3.84 (s, 3 H), 3.82 (s, 3 H), 3.79 (d, J = 3.6 Hz, 2 H), 3.76-3.68 (m, 1 H), 3.38 (dd, J = 4.4, 14.3 Hz, 1 H), 2.72 (d, J = 12.1 Hz, 2 H), 2.15 (s, 3H), 1.83-1.74 (m, 2 H), 1.53-1.45 (m, 3 H), 1.22-1.11 (m, 2 H). NH not visible LCMS (Method 2): [MH+] = 722 at 3.11 min. Chiral analysis (Method 7) at 5.85 min. |
| [(1S)-2-(3,5-dichloro-1-oxido-pyridin-1-ium-4-yl)-1-(3,4-dimethoxyphenyl)ethyl] 4-[[[2-oxo-1-phenyl-2-[[(3S)-quinuclidin-3-yl]methoxy]ethyl]amino]methyl]-benzoate | Example 8 (diastereoisomer 1) | Example 3 | ¹H NMR (400 MHz, CD₃CN) d 8.18 (s, 2H), 8.01 (d, J = 8.1 Hz, 2H), 7.45 (d, J = 8.1 Hz, 2H), 7.42-7.34 (m, 5H), 7.11-7.05 (m, 2H), 6.95 (d, J = 8.1 Hz, 1H), 6.26 (dd, J = 4.5, 9.3 Hz, 1H), 4.37 (s, 1H), 4.13-4.00 (m, 2H), 3.84 (s, 3H), 3.82 (s, 3H), 3.81-3.78 (m, 2H), 3.75-3.67 (m, 1H), 3.37 (dd, J = 4.8, 14.1 Hz, 1H), 2.87-2.79 (m, 1H), 2.75-2.63 (m, 5H), 2.29-2.24 (m, 1H), 1.92-1.83 (m, 1H), 1.55-1.49 (m, 3H), 1.47-1.38 (m, 1H), 1.31-1.23 (m, 1H). LCMS (Method 3): [MH+] = 734 at 2.57 min. Chiral analysis (Method 7) at 3.49 min. |
| [(1S)-2-(3,5-dichloro-1-oxido-pyridin-1-ium-4-yl)-1-(3,4-dimethoxyphenyl)ethyl] 4-[[[2-oxo-1-phenyl-24[(3S)-quinuclidin-3-yl]methoxy]ethyl]amino]methyl]-benzoate | Example 10 (diastereoisomer 2) | Example 3 | ¹H NMR (400 MHz, CD₃CN): δ 8.18 (s, 2 H), 8.01 (d, J = 8.3 Hz, 2 H), 7.45 (d, J = 8.6 Hz, 2 H), 7.41-7.38 (m, 5 H), 7.10-7.04 (m, 2 H), 6.95 (d, J = 8.3 Hz, 1 H), 6.26 (dd, J = 4.5, 9.3 Hz, 1 H), 4.37 (s, 1 H), 4.11-4.02 (m, 2 H), 3.84 (s, 3 H), 3.82 (s, 3 H), 3.80 (d, J = 2.7 Hz, 2 |

| Structure | Reference | Precursor | Analytical Data |
|---|---|---|---|
| | | | H), 3.76-3.68 (m, 1 H), 3.37 (dd, J = 4.7, 14.0 Hz, 1 H), 2.84 (dd, J = 10.4, 13.4 Hz, 1 H), 2.75-2.66 (m, 4 H), 2.25-2.22 (m, 1 H), 1.90-1.79 (m, 1 H), 1.61-1.50 (m, 3 H), 1.45-1.39 (m, 1 H), 1.33-1.27 (m, 1 H). NH not visible.<br>LCMS (Method 3): [MH+] = 734 at 2.57 min. Chiral analysis (Method 7) at 6.54 min. |

Example 9 and Example 11

Single diastereoisomers of [(1S)-2-(3,5-dichloro-1-oxido-pyridin-1-ium-4-yl)-1-(3,4-dimethoxyphenyl) ethyl] 4-[[[1-(3-hydroxyphenyl)-2-[(1-methyl-4-piperidyl)-methoxy]-2-oxo-ethyl]amino]methyl] benzoate (diastereoisomer 1 and 2)

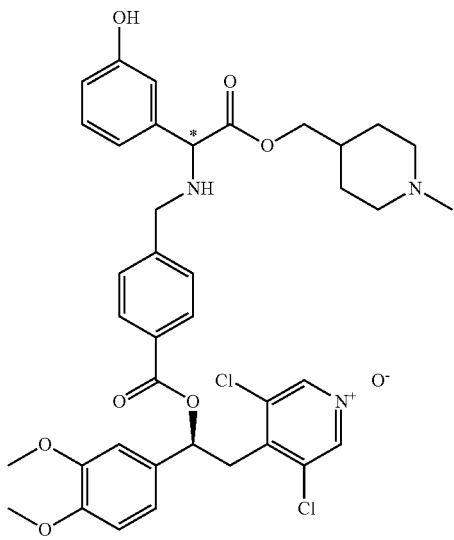

A mixture of [(1S)-2-(3,5-dichloro-1-oxido-pyridin-1-ium-4-yl)-1-(3,4-dimethoxyphenyl)ethyl] 4-formylbenzoate (Intermediate 2, 400 mg, 0.84 mmol), (1-methyl-4-piperidyl)methyl 2-amino-2-(3-hydroxyphenyl)acetate bis hydrobromide (Intermediate 10, 280 mg, 0.64 mmol) and pyridine (79 mg, 1.0 mmol) in EtOH (10 mL) was heated at 60° C. After one hour, NaBH$_3$CN (63 mg, 1.0 mmol) was added and the mixture was stirred for one hour. The solvent was removed in vacuo and the residue was partitioned between H$_2$O (10 mL) and iso-butanol (20 mL). The aqueous phase was extracted with isobutanol (3×20 mL). The combined organic layers were combined and concentrated in vacuo. Purification of the crude material by preparative HPLC afforded the product (130 mg, 28%) as a mixture of diastereoisomers that was submitted directly to chiral preparative SFC to afford the title compound.

Title compound (Example 9, single diastereoisomer 1) was obtained as a white solid (46 mg, 10%).

$^1$H NMR (400 MHz, CD$_3$CN): δ 8.16 (s, 2H), 7.98 (d, J=8.3 Hz, 2H), 7.42 (d, J=8.3 Hz, 2H), 7.17 (dd, J=8.1, 8.1 Hz, 1H), 7.07 (d, J=1.8 Hz, 1H), 7.04 (d, J=2.3 Hz, 1H), 7.03 (dd, J=2.0, 8.3 Hz, 1H), 6.86-6.84 (m, 2H), 6.75-6.72 (m, 1H), 6.23 (dd, J=4.5, 9.6 Hz, 1H), 4.27 (s, 1H), 3.92 (dd, J=3.3, 5.6 Hz, 2H), 3.82-3.78 (m, 1H), 3.81 (s, 3H), 3.79 (s, 3H), 3.76 (d, J=2.4 Hz, 1H), 3.69 (dd, J=9.7, 14.0 Hz, 1H), 3.35 (dd, J=4.5, 14.1 Hz, 1H), 2.80-2.75 (m, 2H), 2.19 (s, 3H), 1.89-1.84 (m, 2H), 1.54-1.47 (m, 3H), 1.29-1.21 (m, 2H), OH and NH not visible.

LCMS (Method 3): [MH+]=738 at 2.47 min. Chiral analysis (Method 7) at 3.13 min.

Title compound (Example 11, single diastereoisomer 2) was obtained as a white solid (28 mg, 6%).

$^1$H NMR (400 MHz, CD$_3$CN): δ 8.17 (s, 2H), 7.98 (d, J=8.1 Hz, 2H), 7.42 (d, J=7.8 Hz, 2H), 7.17 (dd, J=8.1, 8.1 Hz, 1H), 7.08-7.02 (m, 2H), 6.92 (d, J=8.1 Hz, 1H), 6.88-6.84 (m, 2H), 6.74 (d, J=8.1 Hz, 1H), 6.23 (dd, J=4.5, 9.6 Hz, 1H), 4.26 (s, 1H), 3.94-3.89 (m, 2H), 3.82 (s, 3H), 3.80 (s, 3H), 3.76 (s, 2H), 3.69 (dd, J=9.9, 14.0 Hz, 1H), 3.35 (dd, J=4.5, 13.9 Hz, 1H), 2.81-2.74 (m, 2H), 2.19 (s, 3H), 1.91-1.87 (m, 2H), 1.55-1.45 (m, 3H), 1.29-1.22 (m, 2H), OH and NH not visible.

LCMS (Method 3): [MH+]=738 at 2.48 min. Chiral analysis (Method 7) at 4.35 min.

Duration of Action (DoA) Data

Comparison of the DoA of Compound of Example 7 with Compound of Example 7C (Comparative), Demonstrating the Superiority of Example 7 in Terms of DoA as Antibronchospastic Agent.

| Compound | Chemical structure | M3 Ki*** (nM) | M3 IC$_{50}$*** (nM) | sub-maximal inhibition Dose* (nmol/kg) [inhibition at 1 h] | inhibition at 16 h** |
|---|---|---|---|---|---|
| Example 7 Single diastereoisomer 2 of [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate | 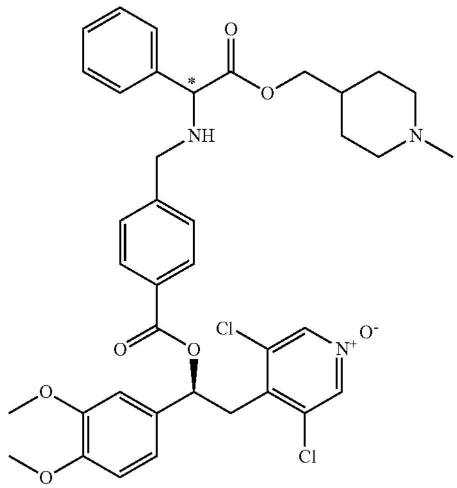 | 0.45 | 0.90 | 30 | >90% |
| Example 7C Diastereoisomer 2 of [(1S)-2-(3,5-dichloro-1-oxido-pyridin-1-ium-4-yl)-1-(3,4-dimethoxyphenyl)ethyl] 4-[[[2-[(1-methyl-4-piperidyl)oxy]-2-oxo-1-phenyl-ethyl]amino]methyl]benzoate | 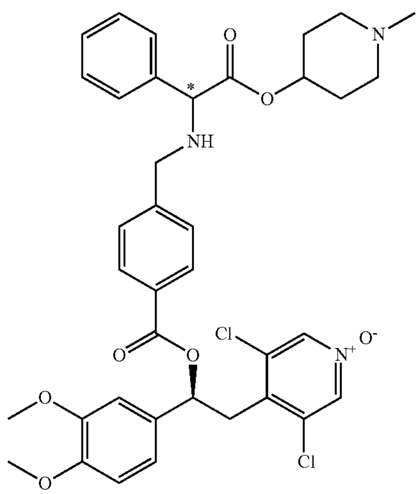 | 0.09 | 0.17 | 3 | <10% |

*Dose producing about 80% (sub-maximal) inhibition of the bronchospasm after 1 h
**16 h after administration of a sub-maximal inhibition dose as indicated in the column on the left
***determined according to the M3 Receptor radioligand binding assay protocol reported below Example 7C Single diastereoisomer 2 of [(1S)-2-(3,5-dichloro-1-oxido-pyridin-1-ium-4-yl)-1-(3,4-dimethoxyphenyl)ethyl] 4-[[[2-[(1-methyl-4-piperidyl)oxy]-2-oxo-1-phenyl-ethyl]amino]methyl]benzoate $^1$H NMR (400 MHz, CD$_3$CN): δ 8.18 (s, 2H), 8.01 (d, J=8.1 Hz, 2H), 7.48-7.33 (m, 7H), 7.10-7.04 (m, 2H), 6.95 (d, J=8.3 Hz, 1H), 6.26 (dd, J=4.5, 9.3 Hz, 1H), 4.78-4.72 (m, 1H), 4.35 (s, 1H), 3.84 (s, 3H), 3.82 (s, 3H), 3.82-3.78 (m, 2H), 3.71 (dd, J=9.6, 14.1 Hz, 1H), 3.37 (dd, J=4.4, 14.0 Hz, 1H), 2.52-2.41 (m, 1H), 2.38-2.08 (m, 4H), 2.14 (s, 3H), 1.88-1.77 (m, 1H), 1.75-1.59 (m, 2H), 1.54-1.44 (m, 1H). LCMS (Method 3): [MH+]=708 at 2.54 min. Chiral analysis (Method 7) at 8.94 min. was obtained as single diastereoisomer, via a similar method as for example 7; starting from 1-methyl-piperidin-4-ol as precursors instead of (1-methyl-4-piperidyl)-methanol.

Protocol of Bronchospasm—Percentage of Inhibition
Animals

Male CD Sprague Dawley rats (220-250 g) were purchased from Charles River Laboratories Italy (Calco, Lecco). Prior to use animals were acclimated for at least 5 days to the local vivarium conditions (room temperature: 20-24° C.; relative humidity: 40-70%), having free access to standard rat chow and softened tap water. All the procedures were performed in animal operating rooms according to ethical guidelines for the conduct of animal research (D. L.vo 116/92).

Treatment with Test Compounds

For the evaluation of potency test compounds were administered intratracheally (i.t.), at different doses in the range 1 nmol/kg-100 nmol/kg, at 1 hour before the induction of experimental bronchospasm. For the assessment of duration of action test compounds were administered intratracheally (i.t.) at 16 hours before the induction of experimental bronchospasm, at the dose showing at 1 h the 80% of inhibition of bronchospasm. Animals were anaesthetized with Urethane (1.2 g/kg, i.p.) and a laryngoscope was moved forward into the mouth to visualize the trachea and guide the insertion of the tip of a custom made small diameter cannula directly into the trachea and located 1-2 mm above the bifurcation. Test compounds were dissolved in 100% dimethyl sulphoxide (DMSO) at $10^{-2}$ M. The target concentration was obtained by dilution of the DMSO stock in saline. Test compounds were instilled locally into the trachea in a volume of 125 μl.

Experimental Procedure

In order to assess the residual inhibitory activity of test compounds at 1 to 16 hours after their administration, rats were surgically prepared. In order to assess the Cch-induced bronchoconstriction in rats, the infusion of physiological solution was stopped and the bronchospastic agent injected into the jugular vein using the same cannula. Soon after washing the cannula with saline to ensure the complete administration of the bronchoconstrictor agent, the saline infusion was started again. Body temperature was kept constant at 37° C. by a heated blanket.

The trachea was cannulated and the lungs were ventilated artificially with a small animal constant volume ventilator (rodent ventilator mod. 7025, Ugo Basile, Comerio, Varese, Italy) at a frequency of 80 strokes/min and at a tidal volume of 2.5 ml/kg. To avoid spontaneous breathing, the animals were injected intravenously (i.v.) with pancuronium bromide (2 mg/kg). Bronchoconstriction was induced by the i.v. injection of Cch 50 μg/kg. In control experiments, repeated injections of this dose produced reproducible short-lasting (1-2 min duration) bronchospasms.

Bronchoconstriction, quantified as a reduction of tidal volume, was evaluated according to the method described by Konzett & Roessler in Konzett H. and Roessler R. (1940). Versuchanornungzu untersuchungen ande bronchial-muskulatur. Arch. Exp. Path. Pharmak.; 195:71-74, which is incorporated herein by reference in its entirety.

Systemic blood pressure and changes in airway resistance were monitored with a digital pressure transducer connected to a bridge amplifier (PowerLab; Ugo Basile, Italy) and recorded using Chart 5 software (Ugo Basile, Italy).

After stabilization of artificial breathing and blood pressure, animals were injected (i.v.) with Cch every 3 min, until 3 stable and reproducible basal responses were obtained. Challenges did not ever exceed the number of 10. The effect of test compounds was expressed as % inhibition of Cch-evoked bronchoconstriction in time-matched, vehicle-treated, animals (controls).

In Vitro Determination of PDE4 Inhibitory Activity

In vitro determination of PDE4 inhibitory activity for compounds of the invention may be determined according to one of the protocols reported below.

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM $MgCl_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye.

Samples are then further incubated for 1 h before plates are read at ex 340 nm and em at 665 nm and 615 nm on an EnVision reader. $IC_{50}$ values are determined from competition curves using a non-linear curve fitting program.

PDE4 Cell Free Assay Protocol

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety.

U937 cells are grown at 37° C., 5% $CO_2$ in RPMI 1640 with GlutaMAX™-I medium supplemented with 10% fetal bovine serum and 100 μg/mL Pen-strep (Gibco).

Cells are harvested and washed twice by centrifugation (150×g, 8 min) in cold PBS. Washed cells are re-suspended in cold Krebs-Ringer-Henseleit buffer at a final concentration $20 \times 10^6$ cells/mL and sonicated. After centrifugation at 15000×g for 20 min, the supernatants are pooled, divided in aliquots and stored at −80° C.

PDE4 activity is determined in cells supernatants by assaying cAMP disappearance from the incubation mixtures.

The concentration of the test compounds ranges between $10^{-12}$ M and $10^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$).

Percentage of inhibition of PDE4 activity is calculated, assuming cAMP disappearance in the absence of inhibitors as 100% and cAMP disappearance in heat inactivated samples as 0%.

The Compounds of the invention, when tested in one of the above reported protocols, displayed an $IC_{50}$ lower than 100 nM.

In Vitro Determination of M3 Antagonism

In vitro determination of M3 antagonism for compounds of the invention may be determined according to one of the protocols reported below.

M3 Receptor Radioligand Binding Assay:

Human $M_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay:

CHO-K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non-selective muscarinic radioligand [$^3$H]-N-methyl scopolamine (*Mol. Pharmacol.* 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 µM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

The compounds of the invention, when tested in one of the above reported protocols, displayed an $IC_{50}$ lower than 100 nM.

The compounds of the invention, displayed an $IC_{50}$ lower than 100 nM, preferred even less than 10 nM or even less than 1 nM, in both PDE4 cell free and M3 binding assays. Compounds having lower activity compared with more active compounds, might be preferred for development having consideration of their pharmacological profile in vivo and specifically when showing the above said improved duration of action.

In the following table $IC_{50}$ data are reported for the compounds tested in the above methods, classified according to the following ranges:
+: M3 $IC_{50}$ in the range 10 to 100 nM
++: M3 $IC_{50}$ in the range 1 to 10 nM
+++: M3 $IC_{50}$<=1 nM
+: PDE4B2 IC50 in the range 10 to 100 nM
++: PDE4B2 IC50 in the range 1 to 10 nM
+++: PDE4B2 IC50<=1 nM

| Example no | M3 IC50 activity* | PDE4B2 IC50 activity** |
|---|---|---|
| 1 | ++ | +++ |
| 2 | ++ | ++ |
| 3 | ++ | ++ |
| 5 | ++ | ++ |
| 7 | +++ | ++ |
| 8 | + | ++ |
| 10 | +++ | ++ |
| 11 | ++ | ++ |

*M3 Receptor radioligand binding assay
**PDE4B2 HTRF assay

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

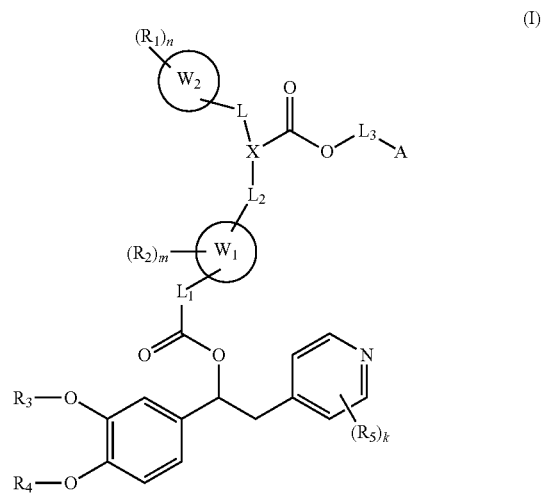

wherein
each $R_1$ is hydrogen, halogen, ($C_1$-$C_4$) alkyl, ($C_1$-$C_4$) alkoxy, ($C_1$-$C_4$) haloalkyl, hydroxy, —$SO_2NR_6R_7$, —CN, —$NR_8SO_2R_9$, —$NR_6R_7$, —$CONR_6R_7$, or —$NR_8COR_9$, wherein said ($C_1$-$C_4$) alkyl is optionally substituted by one or more groups selected from the group consisting of ($C_3$-$C_7$) cycloalkyl, hydroxyl, and —$NR_6R_7$ and wherein said ($C_1$-$C_4$) alkoxy is optionally substituted by one or more halogens ($C_3$-$C_7$) cycloalkyl groups, wherein,
$R_6$ is hydrogen or ($C_1$-$C_6$) alkyl;
$R_7$ is hydrogen or ($C_1$-$C_6$) alkyl;
$R_8$ is hydrogen or ($C_1$-$C_6$) alkyl;
$R_9$ is hydrogen or ($C_1$-$C_6$) alkyl;
n is an integer ranging from 1 to 3;
each $R_2$ is hydrogen, halogen, ($C_1$-$C_4$) alkyl, ($C_1$-$C_4$) alkoxy, ($C_1$-$C_4$)haloalkyl, hydroxy, —$SO_2NR_{10}R_{11}$, —CN, or —$NR_{12}SO_2R_{13}$, wherein said ($C_1$-$C_4$) alkyl and said ($C_1$-$C_4$) alkoxy are optionally substituted by one or more ($C_3$-$C_7$) cycloalkyl groups, wherein
$R_{10}$ is hydrogen or ($C_1$-$C_6$) alkyl;
$R_{11}$ is hydrogen or ($C_1$-$C_6$) alkyl;
$R_{12}$ is hydrogen or ($C_1$-$C_6$) alkyl;
$R_{13}$ is hydrogen or ($C_1$-$C_6$) alkyl;
m is an integer ranging from 1 to 3;
$R_3$ and $R_4$ are the same or different and are each independently:
H;
($C_3$-$C_7$) cycloalkylcarbonyl;
($C_1$-$C_6$) alkyl optionally substituted by one or more substituents selected from the group consisting of ($C_1$-$C_4$) alkoxy, ($C_3$-$C_7$) cycloalkyl, and ($C_5$-$C_7$) cycloalkenyl;
($C_1$-$C_6$) haloalkyl;
($C_3$-$C_7$) cycloalkyl;
($C_5$-$C_7$) cycloalkenyl;
($C_2$-$C_6$) alkenyl; or
($C_2$-$C_6$) alkynyl;

each $R_5$, whenever present, is independently CN, $NO_2$, $CF_3$, or a halogen atom;

k is 0 or an integer ranging from 1 to 3;

$W_1$ is a divalent arylene group;

$W_2$ is an aryl group, a heteroaryl group, or $(C_3-C_7)$ cycloalkyl;

L is a bond or a —$(CH_2)$— group;

$L_1$ is:
  a bond,
  —$(CH_2)_p$—,
  [3]-$(CH_2)_p$—O-[4],
  [3]-$(CH_2)_p$—$NR_{10}$—$(CH_2)_t$-[4],
  [3]-$(CH_2)_p$—OC(O)-[4],
  [3]-$(CH_2)_p$—$NR_{10}$C(O)-[4],
  [3]-$(CH_2)_p$—$NR_{10}$S($O_2$)-[4], or
  [3]-$(CH_2)_p$—S($O_2$)—N($R_{10}$)-[4], wherein [3] and [4] represent, respectively the point of attachment of group $L_1$ to the carbonyl group and to the ring $W_1$ and wherein $R_{10}$ is as described above, p is an integer ranging from 1 to 4 and t is an integer ranging from 1 to 4;

$L_2$ is —$(CH_2)_q$— wherein q is an integer ranging from 1 to 4;

$L_3$ is $(C_1-C_4)$ alkylene;

X is a group of formula $X_1$, $X_2$, or $X_3$:

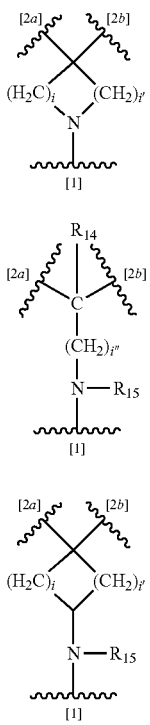

wherein [1] represents at each occurrence the point of attachment of the group X to L2, [2a] represents at each occurrence the point of attachment to L-$W_2$, and [2b] represents at each occurrence the point of attachment to the carbonyl group —$CO_2A$;

and wherein $R_{14}$ is H, OH, $(C_1-C_4)$ alkyl, $(C_1-C_4)$ alkoxy, $(C_1-C_4)$ haloalkyl, or —CN, wherein said $(C_1-C_4)$ alkyl is optionally substituted by one or more groups selected from the group consisting of $(C_3-C_7)$ cycloalkyl, and hydroxyl, or, in alternative, when $R_{14}$ is $(C_1-C_4)$ alkyl, $W_2$ is a phenyl ring, one of $R_1$ is an alkyl in ortho position with respect to L, both $R_1$ and $R_{14}$ may be connected to form with $W_2$ a condensed ring radical selected from the group consisting of 1H-cycloprop-abenzene-1,1-diyl, indane-1,1-diyl (also named as 2,3-dihydro-1H-indene-1,1-diyl), indane-2,2-diyl (also named as 2,3-dihydro-1H-indene-2,2-diyl), 1,2,3,4-tetrahydronaphthalene-1,1-diyl, and 1,2,3,4-tetrahydronaphthalene-2,2-diyl;

$R_{15}$ is hydrogen, $(C_1-C_6)$ alkyl, $(C_3-C_7)$ cycloalkyl, $(C_3-C_7)$ heterocycloalkyl, or benzyl; wherein said $(C_1-C_6)$ alkyl is optionally substituted by hydroxyl or $NR_{18}R_{19}$; said $R_{18}$ and $R_{19}$ being independently hydrogen or $(C_1-C_4)$ alkyl, or, taken together with the nitrogen atom to which they are attached, form a nitrogen containing, saturated heterocycloalkyl group, optionally containing an additional heteroatom selected from O, S, and NH;

and wherein i is 1 or 2;

i' is 1 or 2;

i" is an integer ranging from 0 to 3;

A is a group of formula (i) to (v):

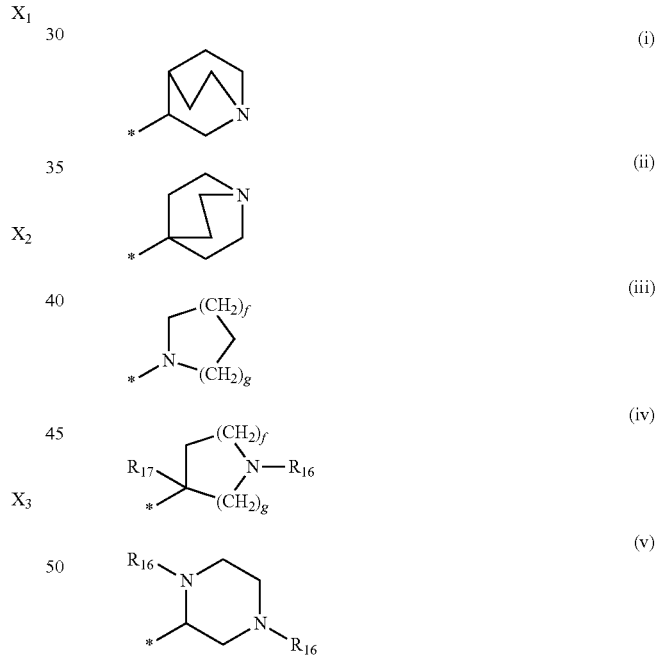

wherein $R_{16}$ is at each occurrence independently $(C_1-C_4)$ alkyl optionally substituted by one or more $(C_1-C_4)$ alkoxy groups; $R_{17}$ is hydrogen, halogen, or $(C_1-C_4)$ alkyl; f=0, 1, 2, or 3; g=0, 1, 2, or 3; and the asterisk (*) represents the point of attachment to the group $L_3$, an N-oxide on the pyridine ring thereof, a deuterated derivative thereof, or a pharmaceutically acceptable salt thereof.

2. A compound, N-oxide, deuterated derivative, or a pharmaceutically acceptable salt according to claim 1 of formula (I)':

53

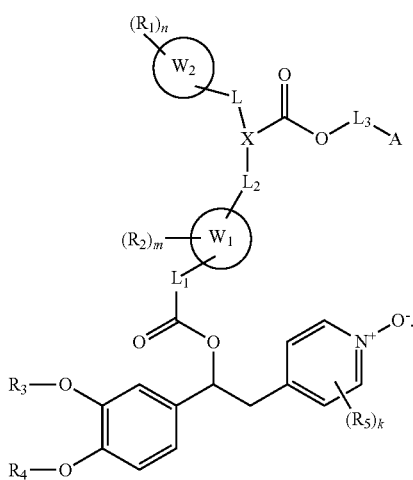

(I)'

3. A compound, N-oxide, deuterated derivative, or a pharmaceutically acceptable salt according to claim 1, wherein A is represented by a group of formula (i), or (iv):

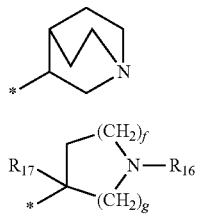

(i)

(iv)

wherein
f=1; g=2; R$_{17}$=is hydrogen; R$_{16}$ is methyl and the asterisk (*) represents the point of attachment to L3 in Formula (I).

4. A compound, N-oxide, deuterated derivative, or a pharmaceutically acceptable salt according to claim 1, wherein X is a group X$_2$, and i" is 0, of formula (IA):

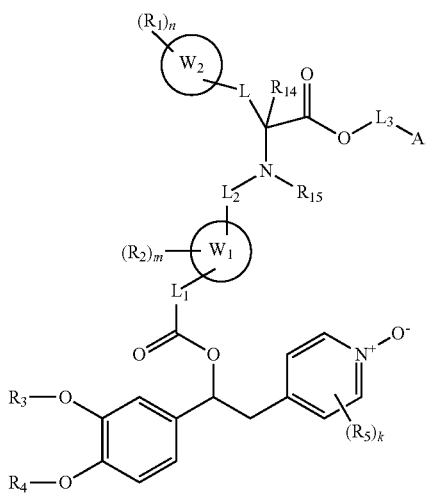

(IA)

54

5. A compound, N-oxide, deuterated derivative, or a pharmaceutically acceptable salt according to claim 4 wherein k is 2 and R$_5$ are halogen atoms.

6. A compound, N-oxide, deuterated derivative, or a pharmaceutically acceptable salt according to claim 5 wherein R$_5$ are two chlorine atoms at positions 3 and 5 of the pyridine ring.

7. A compound, N-oxide, deuterated derivative, or a pharmaceutically acceptable salt according to claim 4, wherein R$_4$ is (C$_1$-C$_6$) alkyl and R$_3$ is (C$_3$-C$_7$) cycloalkyl or (C$_1$-C$_6$) alkyl which is optionally substituted by (C$_3$-C$_7$) cycloalkyl.

8. A compound, N-oxide, deuterated derivative, or a pharmaceutically acceptable salt according to claim 1 of formula (IC):

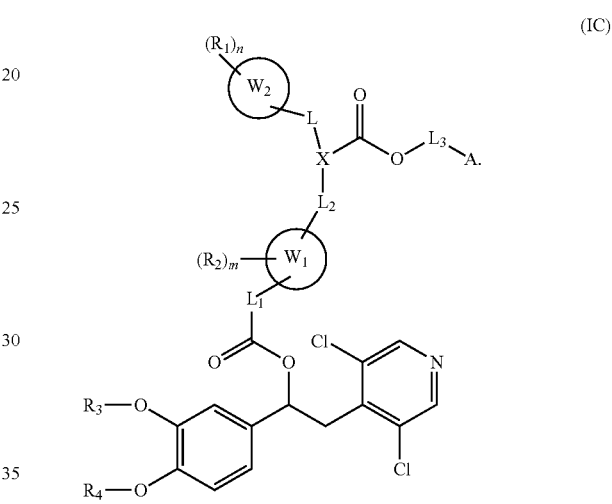

(IC)

9. A compound, N-oxide, deuterated derivative, or a pharmaceutically acceptable salt according to claim 8 of formula (ID):

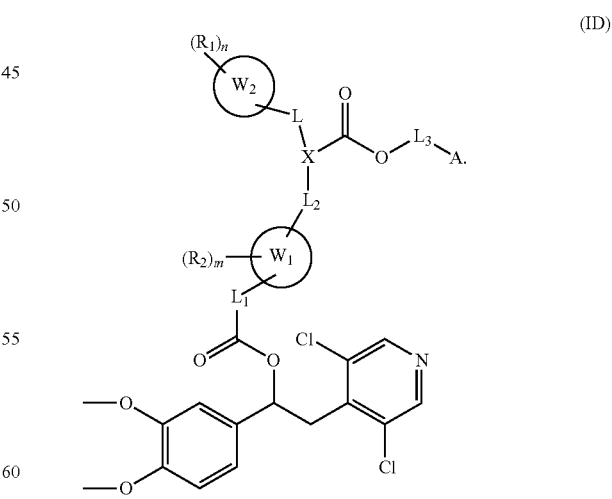

(ID)

10. A compound, N-oxide, deuterated derivative, or a pharmaceutically acceptable salt according to claim 9 wherein:
L$_1$ is a bond and L$_2$ and L$_3$ are both methylene;
m is 0;

$W_1$ is phenylene-1,4-diyl or phenylene-1,3-diyl;
n is 0 or n is 1 and $R_1$ is hydroxyl;
$W_2$ is phenylene;
X is a group of formula $X_1$ wherein both i and i' are 1 or 2, or a group of formula $X_2$ wherein i" is 0 and $R_{14}$ and $R_{15}$ are independently H or methyl, or X is a group of formula $X_3$ wherein both i and i' are 1 and $R_{15}$ is H;
A is a group of formula (i) or (iv):

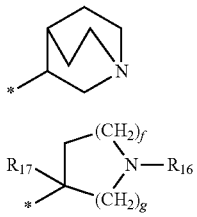

(i)

(iv)

wherein f=1; g=2; $R_{17}$ is hydrogen; $R_{16}$ is methyl and the asterisk (*) represents the point of attachment to $L_3$ in Formula (I).

11. A compound, N-oxide, deuterated derivative, or a pharmaceutically acceptable salt according to claim 1, which has the absolute configuration shown in formula (I)":

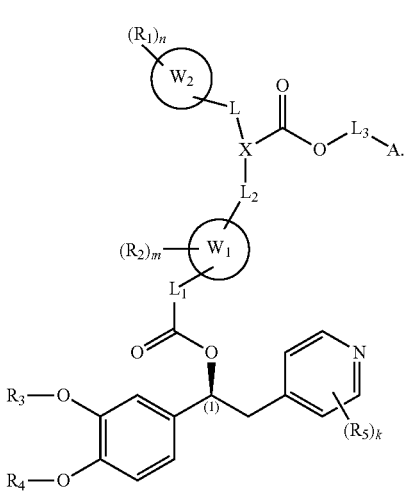

(I)"

12. A compound, N-oxide, deuterated derivative, or a pharmaceutically acceptable salt according to claim 1 which is selected from the group consisting of:

[(1S)-2-(3,5-dichloro-1-oxido-pyridin-1-ium-4-yl)-1-(3,4-dimethoxyphenyl)ethyl] 3-[[[2-[(1-methyl-4-piperidyl)methoxy]-2-oxo-1-phenyl-ethyl]amino]methyl]benzoate;

[(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate;

[(1S)-2-(3,5-dichloro-1-oxido-pyridin-1-ium-4-yl)-1-(3,4-dimethoxyphenyl)ethyl] 4-[[[2-oxo-1-phenyl-2-[[(3S)-quinuclidin-3-yl]methoxy]ethyl]amino]methyl]benzoate;

single diastereoisomer 1 of [(1S)-2-(3,5-dichloro-1-oxido-pyridin-1-ium-4-yl)-1-(3,4-dimethoxyphenyl)ethyl] 3-[[[2-[(1-methyl-4-piperidyl)methoxy]-2-oxo-1-phenyl-ethyl]amino]methyl]benzoate;

single diastereoisomer 2 of [(1S)-2-(3,5-dichloro-1-oxido-pyridin-1-ium-4-yl)-1-(3,4-dimethoxyphenyl)ethyl] 3-[[[2-[(1-methyl-4-piperidyl)methoxy]-2-oxo-1-phenyl-ethyl]amino]methyl]benzoate;

single diastereoisomer 1 of [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate;

single diastereoisomer 2 of [(1S)-2-(3,5-dichloro-1-oxido-pyridin-1-ium-4-yl)-1-(3,4-dimethoxyphenyl)ethyl] 4-[[[2-[(1-methyl-4-piperidyl)methoxy]-2-oxo-1-phenyl-ethyl]amino]methyl]benzoate;

single diastereoisomer 1 of [(1S)-2-(3,5-dichloro-1-oxido-pyridin-1-ium-4-yl)-1-(3,4-dimethoxyphenyl)ethyl] 4-[[[2-oxo-1-phenyl-2-[[(3S)-quinuclidin-3-yl]methoxy]ethyl]amino]methyl]benzoate;

single diastereoisomer 1 of [(1S)-2-(3,5-dichloro-1-oxido-pyridin-1-ium-4-yl)-1-(3,4-dimethoxyphenyl)ethyl] 4-[[[1-(3-hydroxyphenyl)-2-[(1-methyl-4-piperidyl)-methoxy]-2-oxo-ethyl]amino]methyl]benzoate;

single diastereoisomer 2 of [(1S)-2-(3,5-dichloro-1-oxido-pyridin-1-ium-4-yl)-1-(3,4-dimethoxyphenyl)ethyl] 4-[[[2-oxo-1-phenyl-2-[[(3 S)-quinuclidin-3-yl]methoxy]ethyl]amino]methyl]benzoate; and single diastereoisomer 2 of [(1S)-2-(3,5-dichloro-1-oxido-pyridin-1-ium-4-yl)-1-(3,4-dimethoxyphenyl)ethyl] 4-[[[1-(3-hydroxyphenyl)-2-[(1-methyl-4-piperidyl)-methoxy]-2-oxo-ethyl]amino]methyl]benzoate.

13. A pharmaceutical composition, comprising a compound, N-oxide, deuterated derivative, or a pharmaceutically acceptable salt as defined in claim 1 in admixture with one or more pharmaceutically acceptable carriers.

14. A pharmaceutical composition according to claim 13, further comprising another active ingredient selected from the group consisting of a beta2-agonist, an antimuscarinic agent, a corticosteroid, a mitogen-activated protein kinase inhibitor, a nuclear factor kappa-B kinase subunit beta inhibitor, a human neutrophil elastase inhibitor, a phosphodiesterase 4 inhibitor, a leukotriene modulator, a non-steroidal anti-inflammatory agent, and a mucus regulator.

15. A method for the treatment of a disease selected from the group consisting of asthma and COPD, comprising administering an effective amount of a compound, N-oxide, deuterated derivative, or a pharmaceutically acceptable salt according to claim 1 to a subject in need thereof.

16. A method according to claim 15, wherein said disease COPD.

17. A method according to claim 15, wherein said disease is asthma.

* * * * *

UNITED STATES PATENT AND TRADEMARK OFFICE
CERTIFICATE OF CORRECTION

PATENT NO. : 9,597,323 B2
APPLICATION NO. : 15/168438
DATED : March 21, 2017
INVENTOR(S) : Gabriele Amari et al.

Page 1 of 1

It is certified that error appears in the above-identified patent and that said Letters Patent is hereby corrected as shown below:

On the Title Page

The Terminal Disclaimer information has been omitted. Item (45) and the Notice information should read as follows:

--(45) Date of Patent: *Mar. 21, 2017

(*) Notice: Subject to any disclaimer, the term of this patent is extended or adjusted under 35 U.S.C. 154(b) by 0 days.

This patent is subject to a terminal disclaimer.--

Signed and Sealed this
Tenth Day of April, 2018

Andrei Iancu
*Director of the United States Patent and Trademark Office*